United States Patent [19]

Slusarchyk et al.

[11] Patent Number: 4,777,252

[45] Date of Patent: Oct. 11, 1988

[54] 2-OXO-1-[[(SUBSTITUTED SULFONYL)AMINO]-CARBONYL]AZETIDINES

[75] Inventors: William A. Slusarchyk, Belle Mead, N.J.; Peter H. Ermann, Donaustauf, Fed. Rep. of Germany

[73] Assignee: E. R. Squibb & Sons, Inc., Princeton, N.J.

[21] Appl. No.: 85,050

[22] Filed: Aug. 13, 1987

[51] Int. Cl.⁴ ............... A61K 31/415; A61K 31/495; C07D 205/08; C07D 401/14
[52] U.S. Cl. .................. 540/363; 540/360; 540/357; 540/364; 548/318; 548/319; 548/320; 544/295; 544/363; 544/376; 544/383
[58] Field of Search ............ 540/364, 363, 360, 357

[56] References Cited

U.S. PATENT DOCUMENTS

4,587,047 5/1986 Breuer et al. .................. 540/364

FOREIGN PATENT DOCUMENTS

0062876 10/1982 European Pat. Off.
251143 1/1988 European Pat. Off.
2181130 4/1987 United Kingdom.

OTHER PUBLICATIONS

Abstract No. 646 from 1984 ICAAC Meeting: Antimicrobial Activities of 1-Carbacephem Compounds and Their Structure-Activity Relationships", Mochida et al.

*Primary Examiner*—Mark L. Berch
*Attorney, Agent, or Firm*—Lawrence S. Levinson; Donald J. Barrack

[57] ABSTRACT

Antibacterial activity is exhibited by 3-acylamino-2-oxoazetidines having in the 1-position an activating group of the formula $$-\underset{\underset{O}{\|}}{C}-NH-SO_2-R$$

wherein R is and $R_4$ is

20 Claims, No Drawings

2-OXO-1-[[(SUBSTITUTED SULFONYL)AMINO]-CARBONYL]AZETIDINES

DESCRIPTION OF THE INVENTION

Compounds having the formula $$R_1-NH-CH-C(R_2)(R_3)-N(C=O)-C(=O)-NH-SO_2-R \quad \text{I}$$

and pharmaceutically acceptable salts thereof, exhibit antibacterial activity. In formula I, and throughout the specification, the symbols are as defined below.

R is $$-A_1-N\underset{O}{\overset{\phantom{O}}{\diagdown}}N-A_2-\overset{O}{\overset{\|}{C}}-R_4,$$

$$-A_1-N\underset{O\phantom{x}O}{\overset{\phantom{O}}{\diagdown}}N-A_2-\overset{O}{\overset{\|}{C}}-R_4, \text{ or}$$

$$-NH-A_3-\overset{O}{\overset{\|}{C}}-R_4;$$

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, $$-A-\overset{O}{\overset{\|}{C}}-NX_6X_7,$$

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl, $$-O-\underset{X_5}{\overset{X_3}{\overset{|}{C}}}-X_4 \text{ or } -S-\underset{X_5}{\overset{X_3}{\overset{|}{C}}}-X_4$$

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl $$(NH_2-\overset{O}{\overset{\|}{C}}-),$$

(substituted amino)carbonyl, or cyano (—C≡N)], $$-A-\overset{O}{\overset{\|}{C}}-NX_6X_7$$

[wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

$R_4$ is

[chemical structures: chromone/flavone derivatives with OH groups, quinolone derivatives, naphthalene diol derivatives, and pyridone derivative]

$R_5$ is hydrogen or alkyl of 1 to 4 carbon atoms;
$A_1$ is a single bond, $$-NH-\overset{O}{\overset{\|}{C}}-,$$

—NH— or $$-NH-NH-\overset{O}{\underset{\|}{C}}-;$$

$A_2$ is a single bond, —NH—, —CH$_2$—CH$_2$—NH—, or $$-\overset{O}{\underset{\|}{C}}-NH-NH-;$$

$A_3$ is —NH—, —(CH$_2$)$_y$—NH—, $$-NH-\overset{O}{\underset{\|}{C}}-NH-NH-, \quad -\overset{O}{\underset{\|}{C}}-NH-NH-, \quad \text{or} \quad -\overset{CH_2X}{\underset{|}{N}}-$$

wherein X is hydrogen, carboxyl or carbamoyl and y is 2, 3, or 4;

The above symbols (e.g., $A_1$, $A_2$, and $A_3$) are used to represent groups of multiple atoms. These groups are inserted in the structural formulas shown herein in the order in which they are presented (i.e., from left to right). For example, if R is $$-A_1-N\underset{\underset{O}{\|}}{\overset{\frown}{\diagdown}}N-A_2-\overset{O}{\underset{\|}{C}}-R_4,$$

$A_1$ is $$-NH-\overset{O}{\underset{\|}{C}}-,$$

and $A_2$ is —CH$_2$—CH$_2$—NH the R group would be $$-NH-\overset{O}{\underset{\|}{C}}-N\underset{\underset{O}{\|}}{\overset{\frown}{\diagdown}}N-CH_2-CH_2-NH-\overset{O}{\underset{\|}{C}}-R_4$$

not $$-\overset{O}{\underset{\|}{C}}-NH-N\underset{\underset{O}{\|}}{\overset{\frown}{\diagdown}}N-NH-CH_2-CH_2-\overset{O}{\underset{\|}{C}}-R_4.$$

Listed below are definitions of various terms used to describe the β-lactams of this invention. These definitions apply to the terms as they are used throughout the specification (unless they are ortherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The term "halogen" and "halo" refer to fluorine, chlorine, bromine and iodine.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6 or 7-membered heterocycle" (referred to as "$R_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino $$(\overset{O}{\underset{\diagdown}{\diagup}}\overset{CH=N-}{\diagdown}),$$

benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino (—NH$_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins,* edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

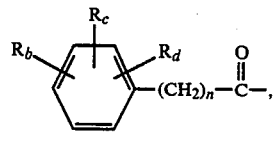

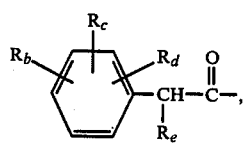

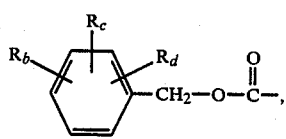

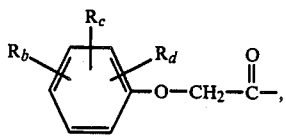

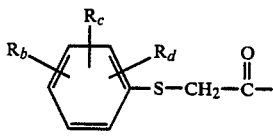

or

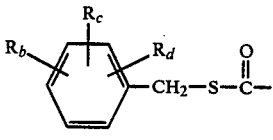

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

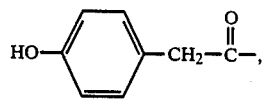

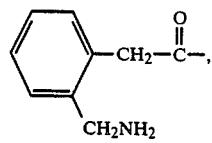

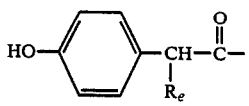

($R_e$ is preferably a carboxyl salt or sulfo salt) and

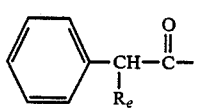

($R_e$ is preferably a carboxyl salt or sulfo salt).

(c) Heteroaromatic groups having the formula

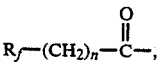

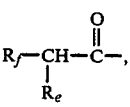

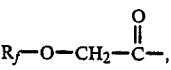

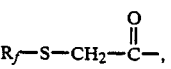

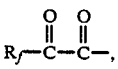

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

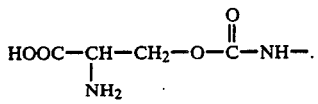

Preferred heteroaromatic acyl groups include those groups of the above formulas wherein $R_f$ is 2-amino-4-thiazolyl, 2-amino-5-halo-4thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

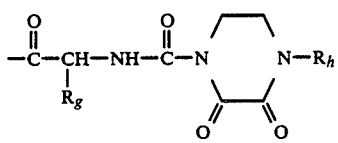

wherein $R_g$ is an aromatic group (including carbocyclic aromatics such as those of the formula

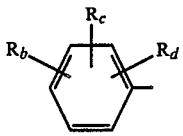

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

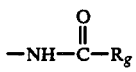

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oximino)arylacetyl groups having the formula

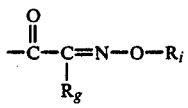

wherein $R_g$ is as defined above and $R_i$ is hydrogen, alkyl, cycloalkyl,

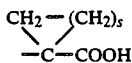

wherein s is 1,2 or 3, 2-pyrrazolylmethyl, (2-oxo-3-pyrrolidinyl)methyl, alkylaminocarbonyl, arylaminocarbonyl (i.e.,

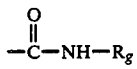

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (includng salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-ethyl, 1-carboxy-1-methylethyl, 2,2,2-trifluoroethyl, 1-carboxycyclopropyl.

(f) (Acylamino)arylacetyl groups having the formula

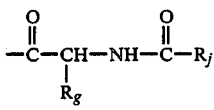

wherein $R_g$ is as defined above and $R_j$ is

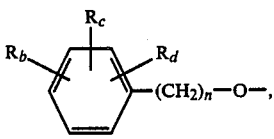

amino, alkylamino, (cyanoalkyl)amino, amido, alkylamido, (cyanoalkyl)amido,

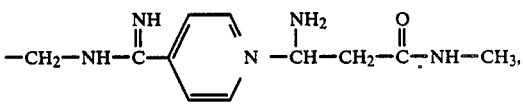

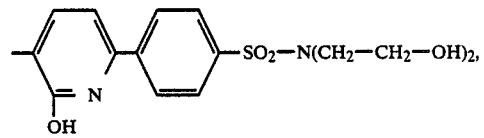

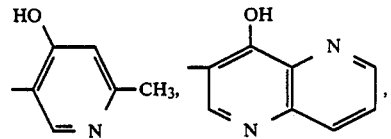

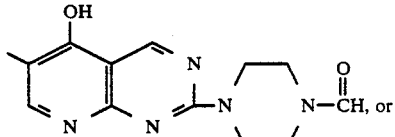

-continued

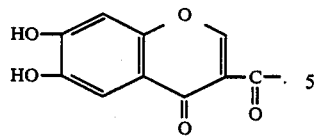

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl-]amino]arylacetyl groups having the formula

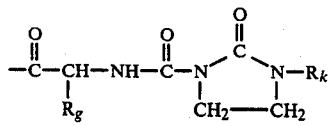

wherein $R_g$ is as defined above and $R_k$ is hydrogen, alkylsulfonyl, arylmethyleneamino (i.e., —N=CH—$R_g$ wherein $R_g$ is as defined above,

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C). Also included within the scope of this invention are racemic mixtures which contain the above-described β-lactams.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

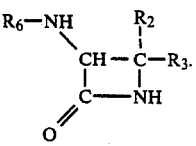

In formula II, and throughout the specification, the symbol "$R_6$" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate having the formula $$O=C=N-SO_2-Y,$$ III wherein Y is a leaving group such as chlorine, yields the corresponding compound having the formula

The reaction is preferably run in an inert organic solvent, e.g., ethyl acetate, tetrahydrofuran, dimethoxyethane, dichloromethane, acetonitrile or mixtures of these solvents. Displacement of the leaving group "Y" with the desired group "R" can be accomplished using the appropriate nucleophile having the formula $$RH,$$ V optionally in the presence of a base (e.g., triethylamine), and yields the corresponding compound having the formula

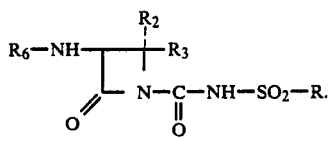

Alternatively, the displacement of the leaving group can be accomplished by reaction of a compound of formula IV with a protected form of a compound of formula V. Following the displacement reaction, the protecting groups can be removed using art-recognized techniques to yield a compound of formula VI.

Protected forms of a compound of formula V include those compounds wherein hydroxyl groups and amino groups are protected. Exemplary protecting groups for the hydroxyl groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis. Exemplary protecting groups for the amino groups are t-butoxycarbonyl, trityl and benzyloxycarbonyl. Removal of the t-butoxycarbonyl or trityl group can be accomplished by treatment with acid (e.g., formic acid or trifluoroacetic acid). Removal of the benzyloxycarbonyl group can be accomplished by catalytic hydrogenation.

Deprotection of a compound of formula VI using conventional techniques yields the corresponding key intermediate having the formula

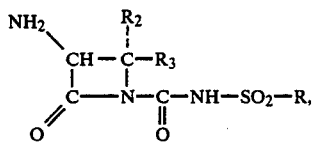

or a salt thereof. The particular deprotection reaction used will, of course, depend on the protecting group ("$R_6$") present. If, for example, $R_6$ is a t-butoxycarbonyl protecting group, deprotection can be accomplished by treatment of a compound of formula VI with acid (e.g., formic acid or trifluoroacetic acid). If, for example, $R_6$ is a benzyloxycarbonyl protecting group, deprotection can be accomplished by catalytic hydrogenation of a compound of formula VI. Alternatively, the $R_6$ protecting group can be removed simultaneously with the other protecting groups immediately following the above-described displacement reaction.

Well known acylation techniques can be used to convert an intermediate of formula VII to a corresponding product of formula I. Exemplary techniques include reaction of a compound of formula VII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

Alternatively, the leaving group "Y" in a compound of formula IV can be displaced with a nucleophile having the formula

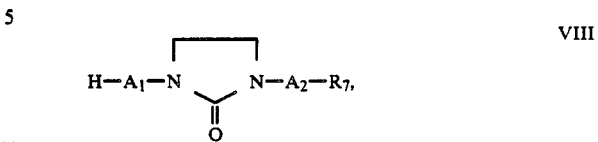

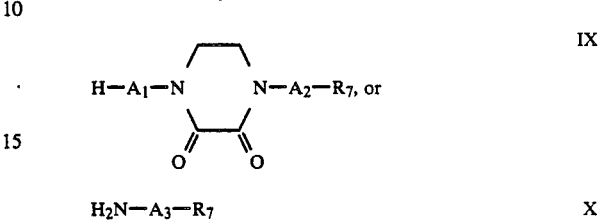

wherein $R_7$ is a protecting group (e.g., t-butoxycarbonyl, trityl, or benzyloxycarbonyl) that is different from the protecting group $R_6$, to give a compound having the formula

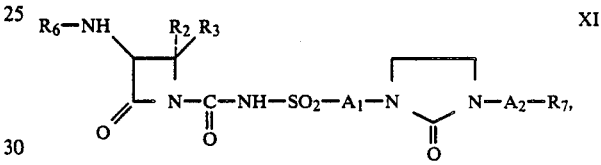

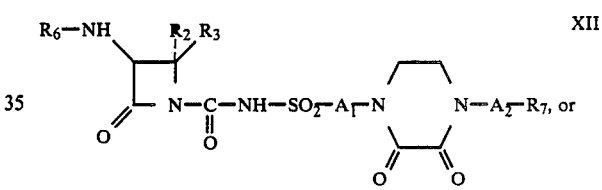

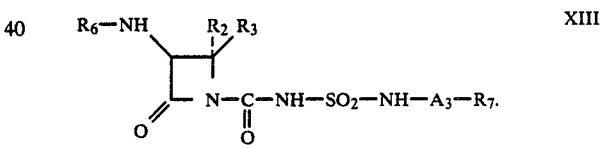

Removal of the protecting group $R_7$ and subsequent coupling with an activated form of a carboxylic acid of the formula

provides the compound of formula VI.

In another alternative, the protecting group $R_6$ in a compound of formula XI, XII, or XIII can be removed and the resulting free amino group can then be acylated with an activated form of carboxylic acid $R_1$—OH to give a compound of the formula

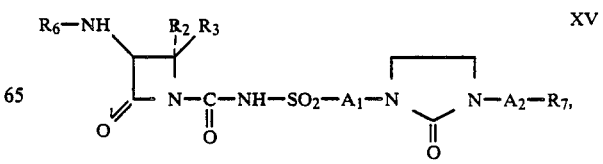

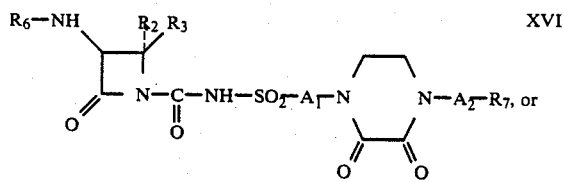 XVI

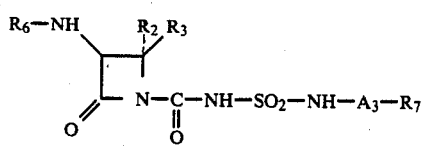 XVII

The amino group $R_7$ can then be removed and the resulting free amino group can be acylated with an activated form of carboxylic acid

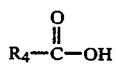

to give a compound of formula I.

An alternative procedure for preparing the compounds of formula I comprises first acylating (acylation techniques have been described above) a 3-amino-2-azetidinone having the formula

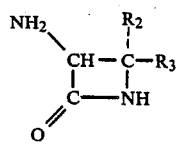 XVIII to yield an intermediate having the formula

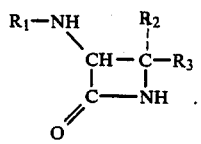 XIX

A

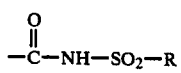

activating group can be introduced in the 1-position of a compound of formula XIX (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

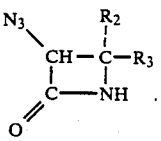 XX

A

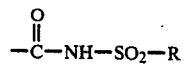

activating group can be introduced in the 1-position of a compound of formula XX (using the procedures described above) to obtain the corresponding compound having the formula

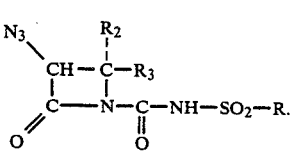 XXI

Reduction of an intermediate of formula XXI yields the corresponding intermediate having the formula

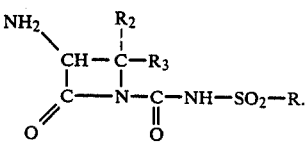 VII

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula XX can be reduced to the corresponding 3-amino-2-azetidinone having the formula

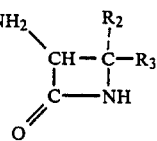 XVIII

The reduction can be accomplished by catalytic (e.g., palladium on charcoal or platinum oxide) hydrogenation or with reducing agents such as zinc or triphenylphosphine. A 3-amino-2-azetidinone of formula XVIII can be reacted as described above (i.e., first acylated and then treated as described above to introduce a

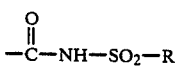

activating group in the 1-position) to yield the products of formula I.

Still another synthesis for preparing the compounds of formula I wherein $R_2$ and $R_3$ are each hydrogen utilizes a 6-acylaminopenicillanic acid having the formula

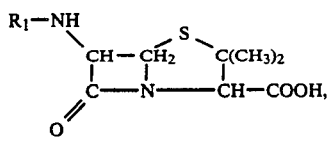

or a salt thereof, as the starting material. By adapting procedures described in the literature, 3-acylamino-2-azetidinone can be obtained from the corresponding 6-acylaminopenicillanic acid of formula XII: see, for example, *Chem. Soc. Special Publication* No. 28, pg. 288 (1977), *The Chemistry of Penicillins,* Princeton University Press, pg. 257, and *Synthesis,* 494 (1977).

As described in the literature 6-acylaminopenicillanic acid, or a salt thereof, can be desulfurized to yield a compound having the formula

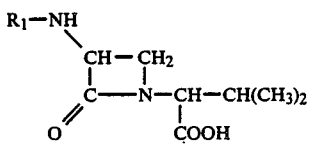

by reduction using Raney nickel. The reaction can be run in water under reflux conditions.

Replacement of the carboxyl group of a compound of formula XXIII with an acetate group followed by hydrolysis yields the corresponding 3-acylamino-2-azetidinone having the formula

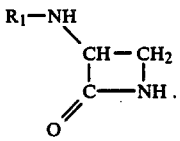

Treatment of a compound of formula XXIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A

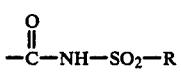

activating group can be introduced in the 1-position of a compound of formula XXIV (yielding products of formula I wherein $R_2$ and $R_3$ are each hydrogen) using the procedures described above.

Still another variation of the above-described synthetic routes for preparing a compound of formula I wherein $R_2$ and $R_3$ are each hydrogen comprises first desulfurizing 6-aminopenicillanic acid, acylating the resulting compound to yield a compound of formula XXIII and then proceeding as described above to obtain first a 3-acylamino-2-azetidinone of formula XXIV and then a product of formula I.

The azetidinones of formula I can also be prepared from amino acids having the formula

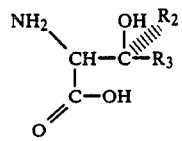

The amino group is first protected (with a protecting group "$R_6$", e.g., t-butoxycarbonyl). The carboxyl group of the protected amino acid is then reacted with an amine having the formula

wherein Z is alkyl, benzyl or triphenylmethyl, in the presence of a carbodiimide to yield a compound having the formula

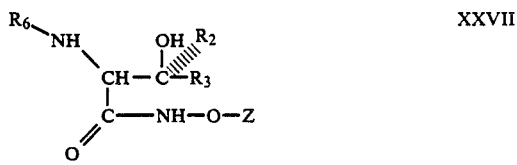

The hydroxyl group of a compound of formula XXVII is converted to a leaving group ("OL") with a reagent, such as methanesulfonyl chloride or pyridine-$SO_3$ complex.

The fully protected compound having the formula

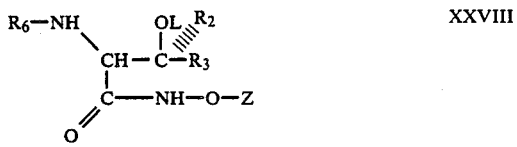

is cyclized by treatment with base, e.g., potassium carbonate. The reaction is preferably carried out in an organic solvent or an organic solvent/water mixture under reflux conditions, and yields a compound having the formula

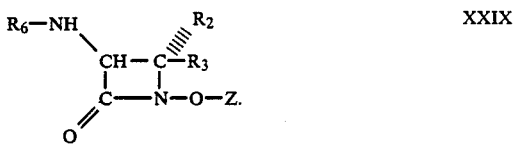

Alternatively, cyclization of a compound of formula XXVII can be accomplished without first converting the hydroxyl group to a leaving group. Treatment of a compound of formula XXVII with triphenylphosphine and diethylazodicarboxylate, yields a compound of formula XXIX.

Exemplary procedures for the conversion of a compound of formula XXVIII to a compound of formula XXIX are described in *J. Amer. Chem. Soc.,* 102, 7026 (1980) and *J. Org. Chem.,* 47, 5160 (1982).

Both of the methods disclosed above for ring closure of a compound of formula XXVII result in the inversion of the stereochemistry at the carbon atom bearing the $R_2$ and $R_3$ substituents when $R_2$ and $R_3$ are not the same.

Removal of the protecting group from the 1-position of an azetidinone of formula XXIX can be accomplished via sodium reduction when Z is alkyl, and yields an intermediate having the formula

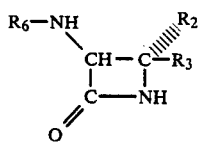

II (at least one of $R_2$ and $R_3$ is hydrogen). If Z is benzyl, catalytic (e.g., palladium on charcoal) hydrogenation will initially yield the corresponding N-hydroxy compound, which upon treatment with titanium trichloride yields an intermediate of formula II. If Z is triphenylmethyl, formic acid or 70% acetic acid/water will initially yield the corresponding N-hydroxy compound.

A

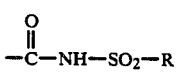

activating group can be introduced in the 1-position of a compound of formula II using the procedures described above, and the resulting compound can be deprotected and acylated.

The nucleophiles of formula V wherein R is

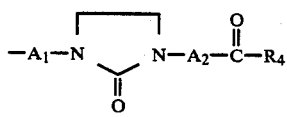

and $A_1$ and $A_2$ are each a single bond can be prepared by reacting a silylated derivative of 2-imidazolidinone

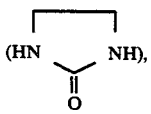

or the anion of 2-imidazolidinone formed with a strong non-nucleophilic base, with an activated, suitably protected or unprotected derivative of carboxylic acid of formula XIV to obtain, upon deprotection, the corresponding compound having the formula

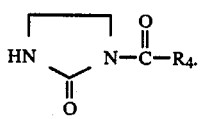

XXX

The reaction can be run in an inert organic solvent such as dimethylformamide, aceonitrile, dichloromethane, or tetrahydrofuran. The acid of formula XIV can be activated with dicyclohexylcarbodiimide, or a combination of dicyclohexylcarbodiimide and hydroxybenzotriazole. An activated and suitably protected derivative of a compound of formula XIV can also be the corresponding acid chloride (prepared with reagents such as phosphorus pentachloride, thionyl chloride, oxalyl chloride or triphenylphosphine/carbon tetrachloride) or a mixed anhydride (prepared with such reagents as diphenylphosphoryl chloride, pivaloyl chloride, or isobutyl chloroformate).

The nucleophile of formula V wherein R is

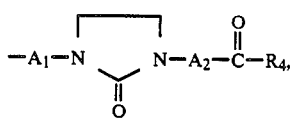

$A_1$ is a single bond and $A_2$ is —NH— can be prepared by reacting an activated and optionally protected derivative of a compound of formula XIV with 1-amino-2-imidazolidinone

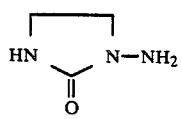

to yield upon deprotection

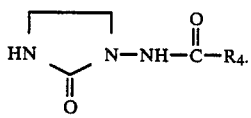

The nucleophiles of formula V wherein R is

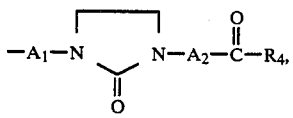

$A_1$ is a single bond and $A_2$ is —CH$_2$—CH$_2$—NH— can be prepared by reacting an activated and optionally protected derivative of a compound of formula XIV with 1-(2-aminoethyl)-2-imidazolidinone

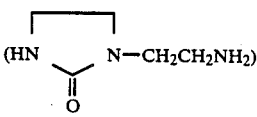

to yield upon deprotection

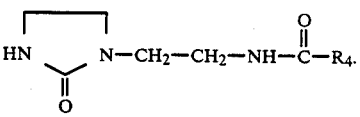

XXXII

The nucleophiles of formula V wherein R is

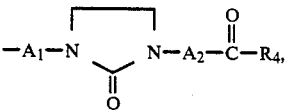

$A_1$ is a single bond and $A_2$ is

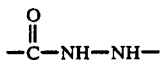

can be prepared by reacting

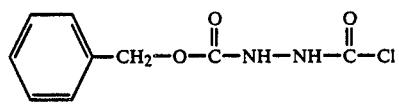
XXXIII with a silylated form of 2-imidazolidinone, the anion of 2-imidazolidinone formed with a strong non-nucleophilic base, or with 2-imidazolidinone in the presence of an organic base to yield

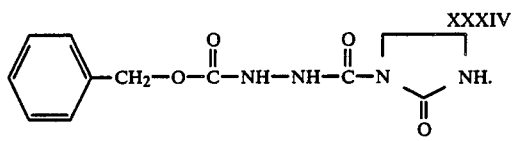
XXXIV

Catalytic hydrogenation of the compound of formula XXXIV yields the compound having the formula

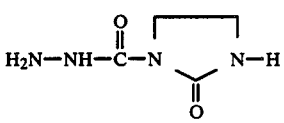
XXXV which can be coupled with an activated and optionally protected derivative of a compound of formula XIV to yield, upon deprotection,

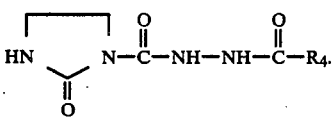
XXXVI

Alternatively, the compound of formula XXXV can be prepared by first reacting 1-chlorocarbonyl-2-imidazolidinone with t-butoxycarbonyl protected hydrazine to yield

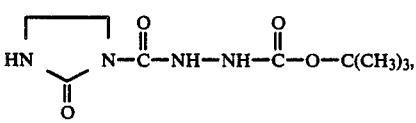
XXXVII and deprotecting the compound of formula XXXVII.

The nucleophiles of formula V wherein R is

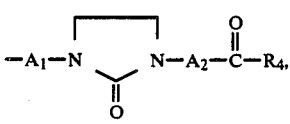

$A_1$ is

and $A_2$ is a single bond can be prepared by reacting a compound having the formula

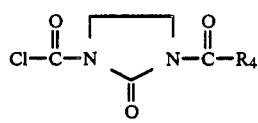
XXXVIII (suitably protected) with hexamethyldisilizane to yield upon hydrolysis and deprotection a compound having the formula

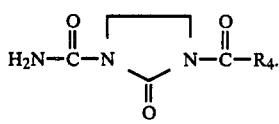
XXXIX

The compounds of formula XXXVIII (suitably protected) can be prepared by reacting a silylated form of a compound of formula XXX (optionally protected) with phosgene.

Alternatively, a compound of formula XXXIX can be prepared by reacting a protected form of a compound of formula XXX with chlorosulfonyl isocyanate followed by hydrolysis of the resulting intermediate and cleavage of the protecting groups.

The nucleophiles of formula V wherein R is

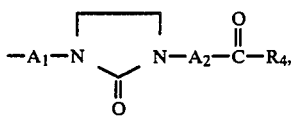

$A_1$ is

and $A_2$ is —NH— can be prepared by reacting a silylated form of the compound

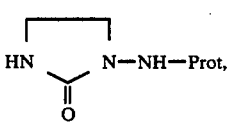
XL wherein the symbol Prot can be an amino protecting group such as t-butoxycarbonyl or benzyloxycarbonyl, with phosgene to yield

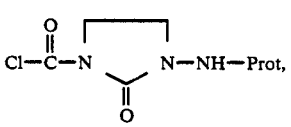
XLI which can be reacted with hexamethylsilazane to yield upon deprotection

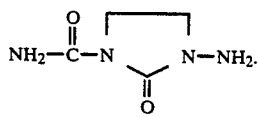  XLII

Reaction of the compound of formula XLII with an optionally protected activated form of a compound of formula XIV yields upon deprotection

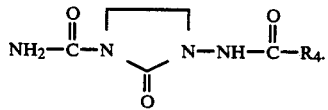  XLIII

Alternatively, a compound of formula XLII can be prepared by reacting the compound having the formula

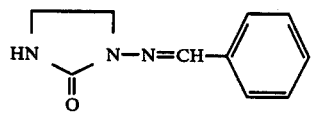  XLIV with chlorosulfonyl isocyanate to yield upon hydrolysis

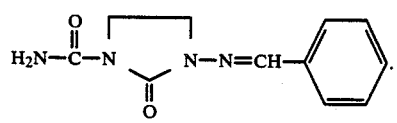  XLV

Treatment of this compound with aqueous acid yields a salt of the compound of formula XLII.

The nucleophiles of formula V wherein R is

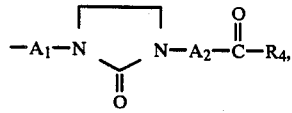

$A_1$ is

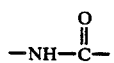

and $A_2$ is —CH$_2$—CH$_2$—NH— can be prepared by first deprotecting 1-(aminocarbonyl)-3-[2-[[(t-butoxy)carbonyl]amino]ethyl]-2-imidazolidinone and coupling the resulting compound with an activated form of a compound of formula XIV (optionally protected) to obtain after deprotection

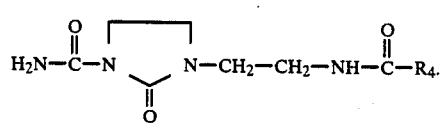  XLVI

The nucleophiles of formula V wherein R is

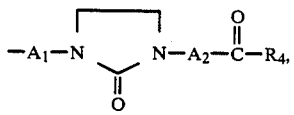, $A_1$ is

and $A_2$ is

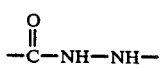

can be prepared by reacting a silylated form of a compound of formula XXXVI (optionally protected) with phosgene followed by hexamethyldisilizane to yield upon hydrolysis and deprotection

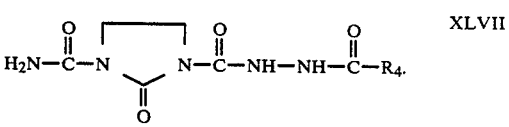  XLVII

Alternatively, a compound of formula XLVII can be prepared by reacting a protected form of a compound of formula XXXVI and chlorosulfonylisocyanate followed by hydrolysis of the resulting intermediate and cleavage of the protecting groups. Alternatively, the compound of formula XXXIV can be reacted with chlorosulfonyl isocyanate followed by hydrolysis of the resulting intermediate to yield

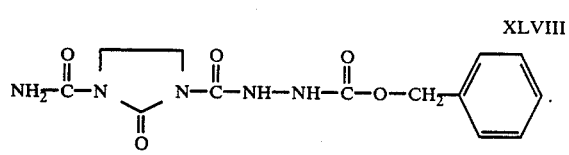  XLVIII

Deprotection of a compound of formula XLVIII by hydrogenolysis yields

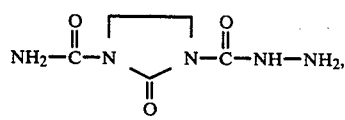  XLIX which can be coupled with an activated and optionally protected derivative of a compound of formula XIV to yield upon deprotection a compound of formula XLVII.

The nucleophiles of formula V wherein R is

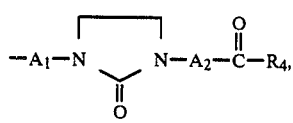, $A_1$ is —NH— and $A_2$ is a single bond can be prepared by coupling the compound of formula XL to an activated form of a compound of formula XIV (optionally protected) and cleaving the protecting group to yield

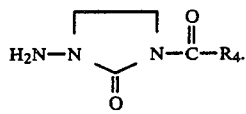   L

The nucleophiles of formula V wherein R is

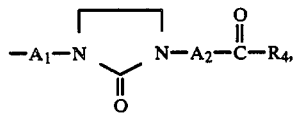

$A_1$ is —NH— and $A_2$ is —NH— can be prepared by coupling a monoprotected (preferably with t-butoxycarbonyl or benzyloxycarbonyl) derivative of 1,3-diamino-2-imidazolidinone with an activated form of a compound of formula XIV (optionally protected) and deprotecting the resulting compound to yield

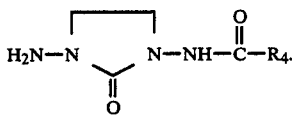   LI

Alternatively, a compound of formula LI can be formed by nitrosating a protected form of a compound of formula XXXI followed by reduction of the nitroso group and cleavage of the protecting groups.

The nucleophiles of formula V wherein R is

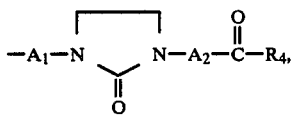

$A_1$ is —NH— and $A_2$ is —CH$_2$—CH$_2$—NH— can be prepared by nitrosating a compound of formula XXXII (suitably protected) to yield a compound having the formula

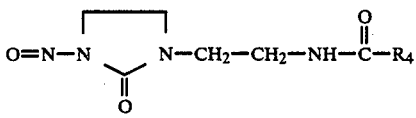   LII (suitably protected) and reducing and deprotecting that compound to yield

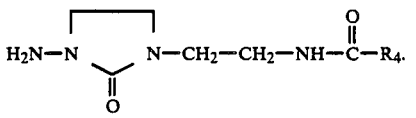   LIII

The neucleophiles of formula V wherein R is

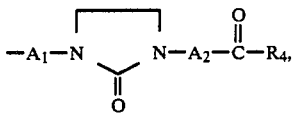

$A_1$ is —NH— and $A_2$ is $$-\overset{O}{\underset{\|}{C}}-NH-NH-$$

can be prepared by nitrosating, reducing and deprotecting a protected derivative of a compound of formula XXXVI. The resulting compound has the formula

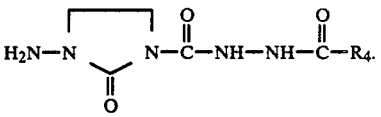   LIV

Alternatively, a compound of formula LIV can be prepared by reacting a compound of formula XL with phosgene to yield

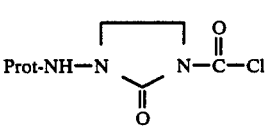   LV which, on reaction with a monoprotected hydrazine in the presence of base, yields

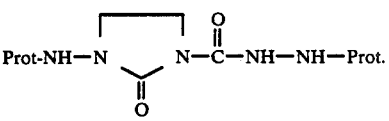   LVI (The two protecting groups must be different). Selective removal of the hydrazide protecting group yields

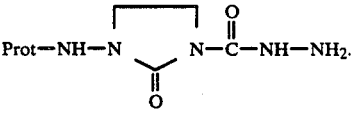   LVII

Coupling of a compound of formula LVII with an activated optionally protected form of a compound of formula XIV, followed by deprotection, yields a compound of formula LIV.

The nucleophiles of formula V wherein R is

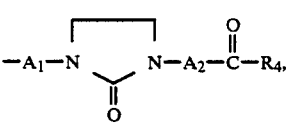

$A_1$ is $$-NH-NH-\overset{O}{\underset{\|}{C}}-$$

and $A_2$ is a single bond can be prepared by reacting a compound of formula XXXVIII (preferably a protected derivative thereof) with hydrazine (preferably in monoprotected form) in the presence of a base or with a silylated form of hydrazine or monoprotected hydrazine to yield a protected derivative of $$H_2N-NH-\overset{O}{\underset{\|}{C}}-N\underset{\underset{\|}{O}}{\diagdown}N-\overset{O}{\underset{\|}{C}}-R_4 \qquad \text{LVIII}$$

which can be deprotected using conventional techniques.

Alternatively, a compound of formula XXXVII (either a silylated derivative thereof or an anion thereof formed by reaction with a strong base) can be reacted with an activated form of a compound of formula XIV (suitably protected) and deprotected to yield a compound of formula LVIII.

The nucleophiles of formula V wherein R is $$-A_1-N\underset{\underset{\|}{O}}{\diagdown}N-A_2-\overset{O}{\underset{\|}{C}}-R_4,$$

$A_1$ is $$-NH-NH-\overset{O}{\underset{\|}{C}}-$$

and $A_2$ is —NH— can be prepared by selective removal of the non-hydrazide protecting group of a compound of formula LVI, followed by coupling with an activated optionally protected compound of formula XIV and subsequent deprotection to yield a compound having the formula $$H_2N-NH-\overset{O}{\underset{\|}{C}}-N\underset{\underset{\|}{O}}{\diagdown}N-NH-\overset{O}{\underset{\|}{C}}-R_4. \qquad \text{LIX}$$

The nucleophiles of formula V wherein R is $$-A_1-N\underset{\underset{\|}{O}}{\diagdown}N-A_2-\overset{O}{\underset{\|}{C}}-R_4,$$

$A_1$ is $$-NH-NH-\overset{O}{\underset{\|}{C}}-$$

and $A_2$ is —CH$_2$—CH$_2$—NH— can be prepared by sequentially reacting a compound of formula XXXII (or a protected derivative thereof) with phosgene followed by hydrazine (or a monoprotected derivative thereof) in the presence of a silylating agent such as N-methyl-N-(trimethylsilyl)trifluoroacetamide to yield upon deprotection $$H_2N-NH-\overset{O}{\underset{\|}{C}}-N\underset{\underset{\|}{O}}{\diagdown}N-CH_2-CH_2-NH-\overset{O}{\underset{\|}{C}}-R_4. \qquad \text{LX}$$

Alternatively, an amino protected derivative of 1-(2-aminoethyl)-2-imidazolidinone (optionally silylated) can be reacted with phosgene, and then with a monoprotected derivative of hydrazine in the presence of a base or a silylating agent (e.g., N-methyl-N-(trimethylsilyl)trifluoroacetamide or bis(trimethylsilyl)acetamide) to yield a protected derivative of the compound having the formula $$H_2N-NH-\overset{O}{\underset{\|}{C}}-N\underset{\underset{\|}{O}}{\diagdown}N-CH_2-CH_2-NH_2. \qquad \text{LXI}$$

The groups used to protect the terminal amino groups in a compound of formula LXI should be chosen so that the protecting group on the aminoethyl group can be selectively removed. The resulting monoprotected compound can be coupled with an activated form of an acid of formula XIV (or a protected derivative thereof) to yield (after deprotection) a compound having the formula $$H_2N-NH-\overset{O}{\underset{\|}{C}}-N\underset{\underset{\|}{O}}{\diagdown}N-\overset{O}{\underset{\|}{C}}-NH-NH-\overset{O}{\underset{\|}{C}}-R_4. \qquad \text{LXIV}$$

The nucleophiles of formula V wherein R is $$-A_1-N\underset{\overset{\|}{O}\ \overset{\|}{O}}{\diagup\diagdown}N-A_2-\overset{O}{\underset{\|}{C}}-R_4$$

can be prepared using the methodology described above for the preparation of the nucleophiles of formula V wherein R is $$-A_1-N\underset{\underset{\|}{O}}{\diagdown}N-A_2-\overset{O}{\underset{\|}{C}}-R_4,$$

but substituting the appropriate 2,3-piperazinedione reactants for the 2-imidazolidinone reactants.

The nucleophiles of formula V wherein R is $$-NH-A_3-\overset{O}{\underset{\|}{C}}-R_4$$

and $A_3$ is —NH— can be prepared by reacting a monoprotected hydrazine with an activated, optionally protected derivative of an acid of formula XIV to obtain, after deprotection, a compound of the formula $$NH_2-NH-\overset{O}{\underset{\|}{C}}-R_4. \qquad \text{LXV}$$

Alternatively, the compounds of formula LXV can be prepared by reacting a carboxylic acid ester of a suitably protected derivative of a compound of formula XIV with hydrazine and then deprotecting.

The nucleophile of formula V wherein R is $$-NH-A_3-\overset{O}{\underset{\|}{C}}-R_4$$

and $A_3$ is —$(CH_2)_y$—NH— can be prepared by reacting a compound of formula $$NH_2-(CH_2)_y-NH_2, \qquad \text{LXVI}$$

optionally monoprotected, with an activated, optionally protected derivative of an acid of formula XIV to obtain, after deprotection, a compound having the formula $$NH_2-(CH_2)_y-NH-\overset{O}{\underset{\|}{C}}-R_4. \qquad \text{LXVII}$$

The nucleophiles of formula V wherein R is $$-NH-A_3-\overset{O}{\underset{\|}{C}}-R_4$$

and $A_3$ is $$-NH-\overset{O}{\underset{\|}{C}}-NH-NH-$$

can be prepared by reacting a compound of formula LXV (suitably protected) with a compound having the formula $$\text{Prot}-NH-NH-\overset{O}{\underset{\|}{C}}-Cl \qquad \text{LXVIII}$$

in the presence of a silylating agent and then removing the protecting groups.

The nucleophiles of formula V wherein R is $$-NH-A_3-\overset{O}{\underset{\|}{C}}-R_4$$

and $A_3$ is $$-\overset{O}{\underset{\|}{C}}-NH-NH-$$

can be prepared by reacting $$NH_2-\overset{O}{\underset{\|}{C}}-NH-NH_2$$

(in the presence of a base or a silylating agent) with an activated, optionally protected derivative of a compound of formula XIV to obtain, after deprotection, a compound having the formula $$NH_2-\overset{O}{\underset{\|}{C}}-NH-NH-\overset{O}{\underset{\|}{C}}-R_4. \qquad \text{LXIX}$$

The nucleophile of formula V wherein R is $$-NH-A_3-\overset{O}{\underset{\|}{C}}-R_4$$

and $A_3$ is $$\underset{-N-}{\overset{CH_2X}{|}}$$

can be prepared by reacting an optionally protected hydrazine derivative of the formula $$NH_2-NH-CH_2-X \qquad \text{LXX}$$

with an activated, optionally protected derivative of an acid of formula XIV to obtain, after deprotection, a compound having the formula $$NH_2-\underset{\underset{}{\overset{|}{N}}}{\overset{CH_2X}{|}}-\overset{O}{\underset{\|}{C}}-R_4. \qquad \text{LXXI}$$

Alternatively, compounds of formula LXXI wherein X is hydrogen can be prepared by reacting methylhydrazine with a carboxylic ester derivative of the acid of formula XIV (or a suitably protected derivative thereof).

The compounds of formula I wherein R is $$-A_1-N\underset{\underset{O}{\overset{\|}{}}}{\overset{\frown}{\phantom{XXX}}}N-A_2-\overset{O}{\underset{\|}{C}}-R_4$$

are preferred. Most preferred are those compounds of formula I wherein R is $$-N\underset{\underset{O}{\overset{\|}{}}}{\overset{\frown}{\phantom{XXX}}}N-NH-\overset{O}{\underset{\|}{C}}\text{-(aromatic group with OH, OH)},$$

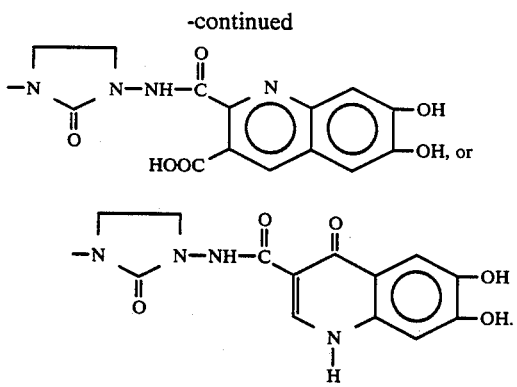

Also preferred are those compounds of formula I wherein $R_1$ is

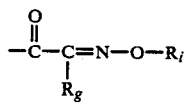

and $R_g$ is 2-amino-4-thiazolyl and $R_1$ is methyl, ethyl, carboxymethyl, 1-carboxy-1-methylethyl, 1-carboxy-1-ethyl or

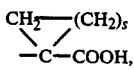

wherein s is 1, 2 or 3. The use of these preferred $R_1$ acyl groups yields a product which exists as the syn or anti isomer or as a mixture of isomers. The syn isomer exhibits greater activity than the anti isomer.

The following examples are specific embodiments of this invention.

EXAMPLE 1

2-[[[1-(2-Amino-4-thiazolyl)-2-[[1-[[[[3-[[(1,4-dihydro-6,7-dihydroxy-4-oxo-3-quinolinyl)carbonyl]amino]-2-oxo-1-imidazolidinyl]sulfonyl]amino]carbonyl]-2-oxo-3-acetidinyl]amino]-2-oxoethylidene]amino]oxy]-2-methylpropanoic acid, disodium salt (A) [[(3,4-Dimethoxyphenyl)amino]methylene]malonic acid, diethyl ester To a solution of 3,4-dimethoxyaniline (100 g, 0.65 mol) in 130 ml of N,N-dimethylformamide was added diethyl ethoxymethylene malonate (141.2 g, 0.65 mol). The mixture was stirred at room temperature for 21 hours. The solvent was evaporated in vacuo and the residual dark brown oil was recrystallized from 1.6 l cyclohexane and 50 g of activated carbon to give 150.5 g of desired product. Extraction of the carbon with hot cyclohexane gave another 27.1 g of product. Total yield 177.6 g, melting point 57°–59° C.

(B) 1,4-Dihydro-6,7-dimethoxy-4-oxo-3-quinolinecarboxylic acid, ethyl ester

[[(3,4-Dimethoxyphenyl)amino]methylene]malonic acid, diethyl ester (60 g, 188.5 mmol) was added to hot diphenylether (bath temperature 275° C.) under stirring. After stirring for 15 minutes, the mixture was allowed to cool to 50° C. The resulting crystals were collected by suction, washed thoroughly with ether and dried in vacuo to yield 34.1 g of the title compound having a melting point of 297° C.

(C) 1,4-Dihydro-6,7-dimethoxy-4-oxo-3-quinolinecarboxylic acid 1,4-Dihydro-6,7-dimethoxy-4-oxo-3-quinolinecarboxylic acid, ethyl ester (68.0 g, 0.245 mol) was suspended in 588 ml of 1N sodium hydroxide solution and stirred for 24 hours at 50°–60° C. To the resulting clear solution dilute hydrochloric acid was added at 0° C. The voluminous precipitate was filtered by suction and washed with water. Drying in vacuo furnished 68.2 g of the title acid, melting point 284.4° C.

(D) 1,4-Dihydro-6,7-dimethoxy-4-oxo-N-(2-oxo-1-imidazolidinyl)-3-quinolinecarboxamide To a suspension of 1,4-dihydro-6,7-dimethoxy-4-oxo-3-quinolinecarboxylic acid (39.9 g, 0.160 mol) in 3.2 l of N,N-dimethylformamide, triethylamine (32.4 g, 0.320 mol) was added. At 0° C. and under nitrogen protection, diphenyl chlorophosphate (43.0 g, 0.160 mol) was added dropwise and the mixture was stirred for 6 hours at 0° C. A solution of N-amino-imidazolidine-2-one (16.2 g, 0.160 mol) in N,N-dimethylformamide was added and stirring was continued at 0° C. overnight. The triethyl ammonium salt (26 g) was filtered off and the filtrate evaporated in vacuo. The residual oil was triturated with 1 l of ethyl acetate and 1 l of water. The resulting solid was filtered off, washed with water and ethyl acetate and dried in vacuo. The crude product was stirred with 270 ml of 0.2N sodium hydroxide solution of 2 days, filtered off, washed with water and dried in vacuo to give 23.2 g of the title compound, melting point>300° C.

(E) 1,4-Dihydro-6,7-dihydroxy-4-oxo-N-(2-oxo-1-imidazolidinyl)-3-quinolinecarboxamide To a suspension of 1,4-dihydro-6,7-dimethoxy-4-oxo-N-(2-oxo-1-imidazolidinyl)-3-quinolinecarboxamide (23.1 g, 69.5 mmol) in 1.2 l of dichloromethane, a solution of boron tribromide (104.5 g, 417 mmol) was added dropwise at 0° C. After stirring for 3 days at room temperature, the precipitate was filtered off, washed with dichloromethane and was then added to 300 ml of methanol under ice cooling. After stirring for 2 hours, the solid was filtered off, washed with methanol and dried in vacuo. Yield: 24.8 g (still contained some starting material). The reaction was repeated to give 18.4 g of the title compound after methanol treatment, melting point>300° C.

(F) [1-[[[[3-[[(1,4-Dihydro-6,7-dihydroxy-4-oxo-3-quinolinyl)carbonyl]amino]-2-oxo-1-imidazolidinyl]sulfonyl]amino]carbonyl]-2-oxo-3-azetidinyl]carbamic acid, phenylmethyl ester To a suspension of 1,4-dihydro-6,7-dihydroxy-4-oxo-N-(2-oxo-1-imidazolidinyl)-3-quinolinecarboxamide (6.09 g, 20 mmol) in 340 ml of dry ethyl acetate were added N-methyl-N-trimthylsilyltrifluoroacetamide (16.0 g, 80 mmol). After stirring for 2 hours, a clear solution was obtained (solution A). To a suspension of (S)-3-[(phenylmethoxy)carbonyl]amino]-2-oxo-1-azetidine (4.40 g, 20 mmol) in 280 ml of dry ethyl acetate, chlorosulfonylisocyanate (3.11 g, 22 mmol) was added.

After stirring for one hour at room temperature, the solution was cooled to 0° C. and solution A was added. After stirring overnight at room temperature, 200 ml of water was added and the resulting precipitate was filtered off by suction and dried in vacuo to give 4.8 g of desired product. From the filtrate, the organic phase was separated and washed with brine. A solid separated which was filtered off, washed with water and dried in vacuo to give an additional 3.4 g of the title compound. Total yield: 8.2 g, melting point 255° C. (dec.).

(G)
2-[[[1-(2-Amino-4-thiazolyl)-2-[[1-[[[[3-[[(1,4-dihydro-6,7-dihydroxy-4-oxo-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester To a solution of [1-[[[[3-[[(1,4-dihydro-6,7-dihydroxy-3-quinolinyl)carbonyl]amino]-2-oxo-1-imidazolidinyl]sulfonyl]amino]carbonyl]-2-oxo-3-azetidinyl]carbamic acid, phenylmethyl ester (3.35 g, 5.3 mmol) in 60 ml of N,N-dimethylformamide, N-methyl-N-trimethylsilyl trifluoroacetamide (5.28 g, 26.5 mmol) was added. After 30 minutes, 1.68 g of palladium on carbon was added, and the mixture was hydrogenolyzed for 1 hour. The catalyst was removed by filtration and the filtrate added to a solution of (Z)-2-amino-α-[[2-(diphenylmethoxy)-1,1-dimethyl-2-oxoethoxy]imino]-4-thiazoleacetic acid, 1-benzotriazole ester (2.96 g, 5.3 mmol) in 30 ml of N,N-dimethylformamide. After stirring for 20 hours, the solvent was distilled off and the residue triturated with 60 ml of water and 75 ml of ethyl acetate. The resulting crystals were filtered off, washed with water and dried in vacuo to give 3.27 g of the title compound.

(H)
2-[[[1-(2-Amino-4-thiazolyl)-2-[[1-[[[[3-[[(1,4-dihydro-6,7-dihydroxy-4-oxo-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt To a mixture of 32 ml of trifluoroacetic acid and 65 ml of anisole, 2-[[[1-(2-amino-4-thiazolyl)-2-[[1-[[[[3-[[(1,4-dihydro-6,7-dihydroxy-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (3.25 g, 3.54 mmol) was added at 0° C. After stirring for 1.75 hours at −2° C., the volatiles were distilled off in vacuo and the oily residue was triturated with dry ether to give a solid which was filtered by suction, washed with ether and dried in vacuo: 3.20 g. This salt was suspended in 35 ml of water and the pH brought to 6.2 with 1N sodium hydroxide solution. Filtration and freeze drying of the filtrate yielded 2.99 g of crude product which was chromatographed on HP20 with water and water:acetonitrile 95:5 as eluent. The water-acetonitrile fractions yielded 0.90 g of the title compound having a melting point >300° C.

EXAMPLE 2
[3S(Z)]-2-[[[1-(2-Amino-4-thiazolyl)-2-[[1-[[[[3-[[(6,7-dihydroxy-4-oxo-4H-benzo[b]pyran-3-yl)carbonyl]amino]-2-oxo-1-imidzolidinyl]sulfonyl]amino]carbonyl]-2-oxo-3-azetidinyl]amino]-2-oxoethylidene]amino]oxy]-2-methylpropanoic acid, dipotassium salt (A) (2-Oxo-1-imidazolidinyl)carbamic acid, 1,1-dimethylethyl ester A mixture of 20.6 g (150 mmol) of 1-amino-2-oxo-1-imidazole hydrochloride salt, 29.2 g (157 mmol) of tributylamine and 103 g (473 mmol) of di-t-butyl dicarbonate was stirred at 100° C. overnight. After cooling, the mixture was evaporated in vacuo and the residue was recrystallized from ethyl acetate to give 19.67 g of the title compound having a melting point of 186°–188° C.

(B) [2-Oxo-3-(trimethylsilyl)-1-imidazolidinyl]carbamic acid, 1,1-dimethylethyl ester While cooling 10.55 g (97.1 mmol) of chlorotrimethylsilane was dropped into a solution of 19.55 g (97.1 mmol) of (2-oxo-1-imidazolidinyl)carbamic acid, 1,1-dimethylethyl ester and 9.83 g (97.1 mmol) of triethylamine in 900 ml of absolute ethyl acetate. After stirring overnight, the salt was filtered off and the filtrate evaporated in vacuo to yield 24.18 g of the title compound; melting point 132.1° C.

(C)
[1-[[[[3-[[(1,1-Dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt Chlorosulfonyl isocyanate (6.13 g, 43.3 mmol) was added to a solution of 8.65 g (39.3 mmol) of (S)-3-[(phenylmethoxy)carbonyl]amino]-2-oxo-1-azetidine in 500 ml of absolute ethyl acetate. After stirring for 30 minutes, 11.83 g (43.3 mmol) of [2-oxo-3-(trimethylsilyl)-1-imidazolidinyl]carbamic acid, 1,1-dimethylethyl ester was added. The mixture was stirred overnight and extracted three times the water. After drying, the ethyl acetate was removed in vacuo. The residue was dissolved in water/methanol (1:1) and the pH adjusted to 6.5 with 1N sodium hydroxide. When the methanol was distilled off in vacuo, the desired product precipitated from the solution. The product was filtered off, washed with water and dried in vacuo; yield: 8.0 g. The filtrate was evaporated to dryness and the residue (14.7 g) was triturated with a small amount of water; yield: 4.4 g. Total yield of pure title compound is 12.4 g having a melting point of 196°–225° C.

(D)
2-[[[1-(2-Amino-4-thiazolyl)-2-[[1-[[[[3-[[(1,1-dimethylethoxy)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester, monosodium salt (Z)-2-Amino-α-[[2-(diphenylmethoxy)1,1-dimethyl-2-oxoethyl]imino]-4-thiazoleacetic acid (2.42 g, 5.5 mmol), 0.84 g (5.5 mmol) of N-hydroxybenzotriazole, and 1.7 g (8.25 mmol) of dicyclohexylcarbodiimide were dissolved in 50 ml of absolute dimethylformamide and stirred for 30 minutes.

(Solution A)

[1-[[[[3-[[(1,1-Dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt (3.02 g, 5.5 mmol) was dissolved in 100 ml of absolute dimethylformamide. After the addition of 1.5 g of palladium on carbon, hydrogen was bubbled through the solution for 40 minutes. The catalyst was filtered off and the filtrate was added dropwise to solution A.

After stirring overnight, dicyclohexylurea was filtered off, the solvent evaporated in vacuo and the residue triturated with ether to afford 4.86 g of crude product.

This material was dissolved in acetone/water and the pH corrected to 6.5. When acetone was distilled off in vacuo, a gummy precipitate separated. The mother liquor was decanted and freeze dried to yield 2.92 g (3.5 mmol) of pure desired product.

(E)
2-[[[1-(2-Amino-4-thiazolyl)-2-[[1-[[[3-amino-2-oxo-1-imidazolidinyl]sulfonyl]amino]carbonyl]-2-oxo-3-azetidinyl]amino]-2-oxoethylidene]amino]oxy]-2-methylpropanoic acid, dipotassium salt 2-[[[1-(2-amino-4-thiazolyl)-2-[[1-[[[[3-[[(1,1-dimethylethoxy)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester, monosodium salt (2.8 g, 3.35 mmol) was suspended in 6.4 ml of anisole and, at −10° C., 12.8 ml of trifluoroacetic acid were added dropwise. After stirring for 2 hours at 0° C., 100 ml of ether was added and the precipitate was collected by filtration and dried in vacuo (2.76 g). The crude product was dissolved in water/methanol, and the pH adjusted to 6.5 with 1N potassium hydroxide. Evaporation of the methanol and freeze drying yielded 3.0 g of crude product which was dissolved in water and chromatographed on an ion exchange resin under mplc-conditions with water as eluent to yield 0.59 g (0.95 mmol) of the title compound.

(F) (2,4,5-Trihydroxyphenyl)ethanone

A mixture of triacetoxybenzene (25.2 g, 0.10 mol) and p-toluenesulfonic acid (19.0 g, 0.10 mol) was heated at 140° C. with stirring under nitrogen for 15 minutes. Then water (150 ml) was added, and the reaction was refluxed for 10 minutes. The solution was cooled to 5° C. for 16 hours. The solid was filtered, washed with water (2×40 ml), and dissolved in ethyl acetate (200 ml). The organic solution was dried over sodium sulfate and filtered through silica gel (60–200 mesh, 200 ml). The desired material was eluted with ethyl acetate (4×200 ml). The fractions were combined and the solvent removed in vacuo to give 11.0 g of the title compound.

(G) [4,5-Bis(acetyloxy)-2-hydroxyphenyl]ethanone

To a solution of (2,4,5-trihydroxyphenyl)ethanone (4.0 g, 0.0238 mol) in pyridine (12 ml) at 0° C. was added acetic anhydride (4.5 ml, 0.0476 mol) in pyridine (1 ml) over 2 minutes. After 10 minutes of stirring, ice water (100 ml) was added and the product oiled out. The water layer was decanted and the product was washed with water and the water decanted (3×30 ml). The residue was dissolved in chloroform (100 ml) and the organic layer was washed with water (20 ml), dried over sodium sulfate, filtered and concentrated in vacuo.

The residue was chromatographed twice on silica gel 60–200 mesh (100 ml) in ethyl acetate:hexane (4:1 to 1:1) to give 2.25 g of the desired product.

(H)
6,7-Bis-(acetyloxy)-4-oxo-4H-1-benzopyran-3-carboxaldehyde

To a solution of [4,5-bis(acetyloxy)-2-hydroxyphenyl]ethanone (2.74 g, 0.0109 mol) in dimethylformamide (10 ml) at −78° C. under nitrogen was added phosphorous oxychloride (3.85 ml, 0.0414 mol) over 15 minutes. The reaction was kept at −78° C. for 15 minutes, 0° C. for 30 minutes and 22° C. for 4 hours. The reaction was poured into ice water (120 ml). The resulting precipitate, A, was stirred for 30 minutes, filtered and washed with water (3×20 ml). The filtrate, A, was extracted with chloroform (2×150 ml) and the organic extracts were combined, washed with water (3×200 ml), dried, filtered, and concentrated in vacuo to give an oily residue, C. The precipitate, A, was dissolved in acetone (50 ml) and the organic solution was dried over sodium sulfate, filtered and concentrated to 20 ml. Crystals formed and hexane (5 ml) was added. The crystals, B, were filtered and dried to give 1.32 g of the title compound, melting point 133°–135° C. The mother liquors from B and the residue, C, were combined and concentrated to dryness. The residue was crystallized from dichloromethane:hexane to give an additional 531 mg of desired product.

(I) 6,7-Diacetoxy-4-oxo-4H-1-benzopyran-3-carboxylic acid

To a solution of 6,7-bis(acetyloxy)-4-oxo-4H-1-benzopyran-3-carboxaldehyde (5.25 g, 0.0181 mol) at 0° C. under nitrogen in ethyl acetate (250 ml) was added sulfamic acid (5.25g, 0.054 mol) in water (100 ml) and sodium chlorite (2.65 g, 0.0181 mol) in water (5 ml plus 5 ml wash). After stirring for one-half hour, more ethyl acetate (100 ml) was added. After 1 hour, the reaction was poured into a separatory funnel and the layers separated. The water layer was extracted with ethyl acetate (50 ml). The organic layers were combined and washed with a saturated sodium chloride solution (3×100 ml), dried over sodium sulfate, filtered and concentrated in vacuo to 50 ml. This solution stood at 0° C. for 1 hour, and the crystals were filtered to give 2.6 g of desired acid (crop 1). The mother liquors were concentrated to 25 ml and after standing 1 hour at 0° C., the crystals were filtered to give an additional 0.44 g of desired acid (crop 2). Crops 1 and 2 were combined to give 3.04 g of the title compound.

(J) 6,7-Hydroxy-4-oxo-4H-1-benzopyran-3-carboxylic acid

To a solution of 6,7-diacetoxy-4-oxo-4H-1-benzopyran-3-carboxylic acid (712 mg, 2.33 mmol) in acetic acid (15 ml) was added concentrated hydrochloric acid (10 ml). The reaction was heated to reflux for 10 minutes and then cooled to 22° C. Water (10 ml) was added to the reaction and the precipitate that formed was collected and washed with water (10 ml) and acetone (2 ml) to give 320 mg of the title compound.

(K)
6,7-Dihydroxy-4-oxo-4H-1-benzopyran-3-carboxylic acid chloride

A suspension of 6,7-dihydroxy-4-oxo-4H-1-benzopyran-3-carboxylic acid (89 mg, 0.401 mol) in thionyl chloride (4 ml) was refluxed for 25 minutes. The reaction was cooled to 40° C. and the thionyl chloride removed under reduced pressure. The residual thionyl chloride was chased with toluene (3×10 ml) to give the desired acid chloride as a residue.

(L)

[3S(Z)]-2-[[[1-(2-Amino-4-thiazolyl)-2-[[1-[[[[3-[[(6,7-dihydroxy-4-oxo-4H-benzo[b]pyran-3-yl)carbonyl]amino]-2-oxo-1-imidazolidinyl]sulfonyl]amino]-carbonyl]-2-oxo-3-azetidinyl]amino]-2-oxoethylidene]amino]oxy]-2-methylpropanoic acid, dipotassium salt To a slurry of 2-[[[1-(2-amino-4-thiazolyl)-2[[1-[[[3-amino-2-oxo-1-imidazolidinyl]sulfonyl]amino]carbonyl]-2-oxo-3-azetidinyl]amino]-2-oxoethylidene]amino]oxy]-2-methylpropanoic acid, dipotassium salt (250 mg, 0.401 mmol) in dry acetonitrile (22 ml) was added trifluoroacetic acid (93 μl, 1.20 mmol) and N-methyl-N-(trimethylsilyl)trifluoroacetamide (1.19 ml, 6.42 mmol) at 0° C. under nitrogen. The reaction was stirred for 20 minutes and 6,7-dihydroxy-4-oxo-4H-1-benzopyran-3-carbonyl chloride from above was added in acetonitrile (5 ml). The reaction was stirred for 3 hours at 0° C. Water (0.5 ml) was added to the reaction, and this was stirred 15 minutes. The reaction was concentrated to 5 ml and triturated with ether (3×25 ml). The residue was dried for 30 minutes and slurried in water (40 ml). The pH was raised to 6.5 with 1N potassium hydroxide, and the clear yellow solution was lyophilized to give 340 mg of solid, which was purified on macroreticular styrene-divinylbenzene copolymer resin (100 ml) in water:acetonitrile (1:0 to 1:1) to give 40 mg of the title compound, melting point >250° C.

(M)

[3S(Z)-2-[[[1-(2-Amino-4-thiazolyl]-2-[[1-[[[[3-[[(6,7-dihydroxy-4-oxo-4H-benzo[b]pyran-3-yl)carbonyl]amino]-2-oxo-1-imidazolidinyl]sulfonyl]amino]-carbonyl]-2-oxo-3-azetidinyl]amino]-2-oxo-ethylidene]amino]oxy]-2-methylpropanoic acid

[3S(Z)[-2-[[[1-(2-Amino-4-thiazolyl]-2-[[1-[[[[3-[[ (6,7-dihydroxy-4-oxo-4H-benzo[b]pyran-3-yl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, dipotassium salt (73 mg) was dissolved in water (2 ml), and the pH was lowered to 2.5 with 1N hydrochloric acid. The material was purified on macroreticular styrene-divinylbenzene copolymer resin (45 ml) in water:acetonitrile (1:0 to 3:2) to give after lyophilization 15 mg of the title compound, melting point >250° C.

EXAMPLE 3

2-[[[1-(2-Amino-4-thiazolyl)-2-[[1-[[[[3-[[(3-carboxy-6,7-dihydroxy-2-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt and 2-[[[1-(2-Amino-4-thiazolyl)-2-[[1-[[[[3-[[(2-carboxy-6,7-dihydroxy-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt (A) 6,7-Dimethoxy-2,3-quinolinedicarboxylic acid A suspension of 26.7 g (80 mmol) of 6,7-dimethoxy-2,3-quinolinedicarboxylic acid, diethyl ester, prepared as described by S. B. Kadin and C. H. Lamphere, J. Org. Chem., 49, 4999 (1984), in 10% sodium hydroxide solution (containing 16 g (400 mmol) of sodium hydroxide) was refluxed for 5 hours. After the filtration of the hot solution, 300 ml of water and subsequently 3N hydrochloric acid were added until the pH reached 1.0. The solids were filtered off by suction, washed thoroughly with water, and dried in vacuo to give 22.4 g of the desired product having a melting point of 264°-266° C.

(B) 6,7-Dihydroxy-2,3-quinolinedicarboxylic acid

A suspension of 8.64 g (31.17 mmol) of 6,7-dimethoxy-2,3-quinolinedicarboxylic acid in 125 ml of aqueous hydrogen iodide solution (57%) was refluxed for 3 hours. After cooling, the precipitate was filtered off by suction, washed with water and dried in vacuo to give 4.7 g (60.5%) of desired acid with melting point >300° C.

(C) 6,7-Dihydroxy-2,3-quinolinedicarboxylic anhydride

To a solution of 4.60 g (18.64 mmol) of 6,7-dihydroxy-2,3-quinolinedicarboxylic acid in 110 ml of dimethylformamide were added 4.19 g (20.31 mmol) of dicyclohexylcarbodiimide (DCC). After stirring overnight, the precipitate (dicyclohexylurea) was filtered off and the filtrate evaporated to dryness. The product thus obtained still contained diacid 6,7-dihydroxy-2,3-quinoline-dicarboxylic acid so that the procedure was repeated with another 1.0 g of dicyclohexylcarbodiimide. After the evaporation of the filtrate to dryness, the residue was triturated with ethyl acetate. Filtration and evaporation of the ethyl acetate yielded 2.38 g of the title compound (contains 1 mol equivalent of dimethylformamide).

(D)

2-[[[1-(2-Amino-4-thiazolyl)-2-[[1-[[[3-[[(3-carboxy-6,7-dihydroxy-2-quinolinyl)carbonyl]amino]-2-oxo-1-imiddazolidinyl]sulfonyl]amino]carbonyl]-2-oxo-3-azetidinyl]amino]-2-oxoethylidene]amino]oxy]-2-methylpropanoic acid, tripotassium salt and 2-[[[1-(2-Amino-4-thiazolyl)-2-[[1-[[[[3-[[(2-carboxy-6,7-dihydroxy-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt To a solution of 0.47 g (0.75 mmol) of 2-[[[1-(2-amino-4-thiazolyl)-2-[[1-[[[[3-amino-2-oxo-1-imidazolidinyl]-sulfonyl]amino]carbonyl]-2-oxo-3-azetidinyl]amino]-2-oxoethylidene]amino]oxy]-2-methylpropanoic acid, dipotassium salt in 10 ml of dimethylformamide was added 0.26 g (0.86 mmol) of 6,7-dimethoxy-2,3-quinoline-dicarboxylic anhydride, and the mixture was stirred overnight at room temperature. After the dimethylformamide was distilled off in vacuo, the residue was dissolved in water and the pH adjusted to 6.5 with 1N potassium hydroxide. Freeze drying yielded 0.76 g of crude product which was purified by column chromatography on XAD resin under mplc conditions with water as eluent to give 0.12 g of 2-[[[1-(2-amino-4-thiazolyl)-2-[[1-[[[[3-[[(3-carboxy-6,7-dihydroxy-2-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt, melting point 240°-280° C., dec., and 0.21 g of a mixture of 2-[[[1-( 2-amino-4-thiazolyl)-2-[[1-[[[[3-[[(3-carboxy-6,7-dihydroxy-2-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt and 2-[[[1-(2-amino-4-thiazolyl)-2-[[1-[[[[3-[[(2-carboxy-6,7-dihydroxy-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, tripotassium salt in a ratio of ca. 2:1.

EXAMPLE 4

[3S(Z)-2-[[[1-(2-Amino-4-thiazolyl)-2-[[1-[[[[2-[(6,7-dihydroxy-2-naphthalenyl)carbonyl]hydrazino]sulfonyl]amino]carbonyl]-2-oxo-3-azetidinyl]amino]-2-oxoethylidene]amino]oxy]-2-methyl propanoic acid, disodium salt (A) 6,7-Dimethoxy-2-naphthalenecarbonyl chloride To a suspension of 3.0 g (12.9 mmol) of 6,7-dimethoxy-2-naphthalenecarboxylic acid in 20 ml of dry dichloromethane was added 3.1 g (14.8 mmol) of phosphorus pentachloride at 0° C. After two hours, the solution was filtered and evaporated in vacuo. The residue was dried and triturated with ether/hexane (1:1) to give 2.47 g of the desired acid chloride.

(B) 6,7-Dimethoxy-2-naphthalenecarboxylic acid, 2-(2,2-dimethyl-1-oxopropyl)hydrazide To a solution of 1.3 g (9.8 mmol) of t-butyl carbazate and 2.0 g (19.7 mmol) of triethylamine in 70 ml of ethyl acetate, was added dropwise at room temperature 2.47 g (9.8 mmol) of 6,7-dimethoxy-2-naphthalenecarbonyl chloride in 60 ml of ethyl acetate. After stirring for one additional hour, the mixture was washed with 10% hydrochloric acid, water and brine and dried over magnesium sulfate. Ethyl acetate was evaporated in vacuo to yield 1.5 g of the title compound.

(C) 6,7-Dihydroxy-2-naphthalenecarboxylic acid, hydrazide

At −78° C., 3.5 g (14.2 mmol) of boron tribromide (0.5M in dichloromethane) was added dropwise to a solution of 1.59 g (4.7 mmol) of 6,7-dimethoxy-2-naphthalenecarboxylic acid, 2-(2,2-dimethyl-1-oxopropyl)-hydrazide in 40 ml of dry dichloromethane. The solution was allowed to warm to room temperature and was stirred overnight. 30 ml of water and 115 ml of ether were added and the resulting precipitate filtered, washed and dried in vacuo to give 0.42 g of the title compound as its hydrobromide salt. The salt was dissolved in water and treated with one equivalent of sodium bicarbonate solution to give, after precipitation and collection by filtration, 0.22 g of the desired title compound.

(D) 6,7-Dihydroxy-2-naphthalenecarboxylic acid, 2-[[[[3-[[(phenylmethoxy)carbonyl]amino]-2-oxo-1-azetidinyl]carbonyl]amino]sulfonyl]hydrazide N-Methyl-N-trimethylsilyltrifluoroacetamide (20.0 g, 100 mmol) was added to a suspension of 10.9 g (50 mmol) of 6,7-dihydroxy-2-naphthalene-carboxylic acid, hydazide in 150 ml of ethyl acetate, and for 4.5 hours, the mixture was heated to 55°–60° C. The clear solution was evaporated to dryness and the crystalline residue was dissolved in 120 ml of ethyl acetate (solution A).

Chlorosulfonyl isocyanate (7.1 g, 50 mmol) was added to a suspension of 11.0 g (50 mmol) of (S)-3-[[(phenylmethoxy)carbonyl]amino]-2-oxo-1-azetidine in 350 ml of ethyl acetate. After stirring for 1 hour at room temperature, the solution was cooled to 0° C., and 150 ml of dichloromethane and 15.0 g (150 mmol) of triethylamine was added (solution B).

To solution B, solution A was added at 0° C. After stirring for 40 hours at room temperature, the mixture was poured on ice water. The aqueous phase was washed twice with 75 ml portions of ethyl acetate and then layered with 250 ml of ethyl acetate. The pH (8.8) was adjusted to 2 using 2N hydrochloric acid. The aqueous phase was extracted twice with ethyl acetate, and the combined acidic ethyl acetate extracts were washed with brine, dried (sodium sulfate), and evaporated in vacuo to a crystalline solid. Trituration with ether gave 17.4 g of the title compound.

(E) 6,7-Dihydroxy-2-naphthalenecarboxylic acid, 2-[[[(3-amino-2-oxo-1-azetidinyl)carbonyl]amino]sulfonyl]hydrazide, trifluoroacetate (1:1) salt 6,7-Dihydroxy-2-naphthalenecarboxylic acid, 2-[[[3-[[(phenylmethoxy)carbonyl]amino]-2-oxo-1-azetidinyl]-carbonyl]amino]sulfonyl]hydrazide (5.94 g, 11 mmol) was added at 0° C. to a mixture of 27 ml of trifluoroacetic acid and 7 ml of thioanisole. The mixture was stirred overnight at 10° C. and then added to 150 ml of ether. The precipitate was filtered, washed with ether and petroleum ether and dried in vacuo. The crude product (6.6 g) was suspended in 50 ml of isopropanol and thoroughly stirred for 1.5 hours. The product was filtered off, washed with isopropanol and ether and dried in vacuo to give 3.8 g of the title compound.

(F) 6,7-Dihydroxy-2-naphthalenecarboxylic acid, 2-[[[[3-[[(2-amino-4-thiazolyl)[[2-(diphenylmethoxy)-1,1-dimethyl-2-oxoethoxy]imino]acetyl]amino]-2-oxo-1-azetidinyl]carbonyl]amino]sulfonyl]hydrazide 1.2 g (12 mmol) Triethylamine and, at −30° C. (under nitrogen protection), 1.1 g (4 mmol) of diphenyl chlorophosphate was added to a solution of 1.76 g (4 mmol) of (Z)-2-amino-α-2-[[2-(diphenylmethoxy)-1,1-dimethyl-2-oxoethoxy]imino]-4-thiazoleacetic acid in 40 ml of dry dimethylformamide. After stirring for 1 hour at −30° C., 0.8 g (8 mmol) of triethylamine and 2.1 g (4 mmol) of 6,7-dihydroxy-2-naphthalenecarboxylic acid, 2-[[[(3-amino-2-oxo-1-azetidinyl)carbonyl]amino]sulfonyl]hydrazide, trifluoroacetate (1:1) salt was added. The solution was then stirred for 2 hours at −10° C., and 1.5 hours at 0° C. The dimethylformamide was then distilled off in vacuo and 70 ml of ethyl acetate and 30 ml of ice water was added to the residual oil. When the pH was then brought to 1.5 with 2N hydrochloric acid, an oil separated which was isolated, dissolved in acetone and dropped into water to give a crystalline material. The crystals were filtered off, washed with water and ether and dried in vacuo to give 0.8 g of crystalline desired product.

The aqueous layer was extracted twice with ethyl acetate (20 ml), and the combined organic phase was washed with 20 ml of 1N hydrochloric acid and twice with 20 ml of water. After drying (sodium sulfate) and evaporating of the ethyl acetate, the product was triturated with ether to give an additional 2.39 g of desired product as a solid. The total yield of the title compound was 3.19 g.

(G)
[3S(Z)]-2-[[[1-(2-Amino-4-thiazolyl)-2-[[1-[[[[2-[(6,7-dihydroxy-2-naphthalenyl)carbonyl]hydrazino]sulfonyl]amino]carbonyl]-2-oxo-3-azetidinyl]amino]-2-oxoethylidene]amino]oxy]-2-methylpropanoic acid, disodium salt Trifluoroacetic acid (22 ml) was added at −10° C. to a suspension of 2.2 g (2.65 mmol) of 6,7-dihydroxy-2-naphthalenecarboxylic acid, 2-[[[[3-[[(2-amino-4-thiazolyl)[[2-(diphenylmethoxy)-1,1-dimethyl-2-oxoethoxy]imino]acetyl]amino]-2-oxo-1-azetidinyl]carbonyl]amino]sulfonyl]hydrazide in 4.4 ml of anisole. After stirring for 1 hour, 80 ml of ether was added at −10' C.; the resulting precipitate was filtered, washed with ether and petroleum ether and dried.

The crude product (1.2 g) was suspended in 50 ml of water and then the pH was adjusted to 6.2 with 1N sodium hydroxide. After freeze drying, the material was chromatographed on HP20 with water as eluent. Freeze drying yielded 0.40 g of the title compound having a melting point >300° C.

EXAMPLE 5
[3S(Z)]-2-[[[3-[[[[3-[[(2-Amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-3-quinolinecarboxylic acid, disodium salt and
[3S(Z)]-3-[[[3-[[[[3-[[(2-Amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-2-quinolinecarboxylic acid, disodium salt

(A)
[3-[[[[3-[[(2-amino-4-thiazolyl)(methoxyimino)acetyl]amino]-2-oxo-1-azetidinyl]carbonyl]amino]sulfonyl]-2-oxo-1-imidazolidinyl]carbamic acid, 1,1-dimethylethyl ester, monosodium salt To a solution of 8.23 g (15 mmol) [1-[[[3-[[(1,1-dimethylethoxy)carbonyl]amino]-2-oxo-1-imidazolidinyl]sulfonyl]amino]carbonyl]-2-oxo-3-azetidinyl]carbamic acid, phenylmethyl ester, monosodium salt in 275 ml of dimethylformamide was added 4.1 g of palladium on carbon and hydrogen was bubbled through the mixture for 40 minutes. The catalyst was filtered off and to the filtrate was added a solution of 4.77 g (15 mmol) of (Z)-(2-amino-4-thiazolyl)(methoxyimino)acetic acid, 1-benzotriazole ester in 135 ml of dimethylformamide. After stirring overnight, the dimethylformamide was evaporated in vacuo and the residue triturated with ether. The resulting crystalline material was filtered off, washed with ether and dried in vacuo to give 9.85 g of the title compound.

(B)
2-Amino-N-[1-[[[(3-amino-2-oxo-1-imidazolidinyl)sulfonyl]amino]carbonyl]-2-oxo-3-azetidinyl]-α-(methoxyimino)-4-thiazoleacetamide, monosodium salt To a solution of 4.79 g (8 mmol) of [3-[[[[3-[[(2-amino-4-thiazolyl)(methoxyimino)acetyl]amino]-2-oxo-1-azetidinyl]carbonyl]amino]sulfonyl]-2-oxo-1-imidazolidinyl]carbamic acid, 1,1-dimethylethyl ester, monosodium salt in 15 ml of anisole was added dropwise at 30.5 ml of trifluoroacetic acid at 0° C. After stirring for 2 hours, anisole and trifluoroacetic acid were distilled off and the residue was triturated with ether. The crystals were filtered off and dried to yield 4.26 g of crude material which was dissolved in methanol/water (1:1). The pH was adjusted to 6.5 with 1N sodium hydroxide and after the evaporation of the methanol, the aqueous solution was freeze dried. Yield 4.39 g. This material was chromatographed in three portions (each 1.4 g) on XAD with water as eluent under mplc conditions to give 1.36 g of the title compound.

(C)
[3S(Z)]-2-[[[3-[[[[3-[[(2-Amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-3-quinolinecarboxylic acid, disodium salt and
[3S(Z)]-3-[[[3-[[[[3-[[(2-Amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-2-quinolinecarboxylic acid, disodium salt To a solution of 0.45 g (1.0 mmol) 2-amino-N-[1-[[[(3-amino-2-oxo-1-imidazolidinyl)sulfonyl]amino]-carbonyl]-2-oxo-3-azetidinyl]-α-(methoxyimino)-4-thiazoleacetamide, monosodium salt in 10 ml of dimethylformamide was added 0.36 g (1.1 mmol) of 6,7-dihydroxy-2,3-quinolinedicarboxylic anhydride. After stirring overnight at room temperature, the dimethylformamide was evaporated in vacuo. The residue was dissolved in water and after the pH was brought to 6.5 with dilute sodium hydroxide, the mixture was freeze dried (0.84 g). Column chromatography on XAD under mplc conditions with water as eluent yielded 0.10 g of [3S(Z)]-2-[[[3-[[[[3-[[(2-amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-ddihydroxy-3-quinolinecarboxylic acid, disodium salt and 0.14 g of a mixture of [3S(Z)]-2-[[[3-[[[[3-[[(2-amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-3-quinolinecarboxylic acid, disodium salt and [3S(Z)]-3-[[[3-[[[[3-[[(2-amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-2-quinolinecarboxylic acid, disodium salt in a ratio of 1:1.

EXAMPLE 6
[3S(Z)]-2-[[[1-(2-Amino-4-thiazolyl)-2-[[1-[[[[3-[[(7,8-dihydroxy-4-oxo-4H-pyrido[1,2-a]pyrimidin-3-yl)carbonyl]amino]-2-oxo-1-imidazolidinyl]sulfonyl]amino]-carbonyl-2-oxo-3-azetidinyl]amino]-2-oxoethylidene]amino]oxy]-2-methylpropanoic acid, disodium salt (A) 4,5-Bis(phenylmethoxy)-2-pyridinecarboxylic acid, phenylmethyl ester 21.5 g (156 mmol) of potassium carbonate was added to a suspension of 29.4 g (120 mmol) of 1,4-dihydro-5-(phenylmethoxy)-4-oxo-2-pyridinecarboxylic acid in 350 ml of N,N-dimethylformamide (DMF) and stirred for 1 hour at room temperature. 31 ml (264 mmol) of benzylbromide was added and the mixture was heated at 100° C. under stirring for 25 hours. After cooling to room temperature, the DMF was distilled off in vacuo and the residue triturated with ethyl acetate with short heating to 60° C. 40 g of inorganic salts were filtered off, the filtrate was concentrated to ca. 75 ml and chromatographed on silica gel with ethyl acetate:petroleum ether 90:10 as eluent. Yield: 35.5 g; melting point 116.7° C.

(B) 4,5-Bis(phenylmethoxy)-2-pyridinecarboxylic acid

To a solution of 11.8 g (28 mmol) of 4,5-bis(phenylmethoxy)-2-pyridinecarboxylic acid, phenylmethyl ester in 115 ml of tetrahydrofuran were added 16 ml water and 35 ml of 1N potassium hydroxide. After stirring overnight at room temperature, 115 ml water was added and the pH was adjusted to 2.5 with 1N hydrochloxic acid. The acid was filtered off, washed with water and dried in vacuo. Yield: 8.6 g; melting point 203.6° C.

(C) [4,5-Bis(phenylmethoxy)-2-pyridinyl]carbamic acid, 1,1-dimethylethyl ester

To a suspension of 1.5 g (4.5 mmol) of 4,5-bis(phenylmethoxy)-2-pyridinecarboxylic acid in 25 ml of t-butanol were added 1.5 g (5.4 mmol) of diphenylphosphoryl azide and 0.54 g (5.4 mmol) of triethylamine. The mixture was stirred at 80° C. for 17 hours. After cooling to room temperature, the crystals were filtered off, washed with ether and dried in vacuo. Yield: 1.3 g. Concentration of the mother liquor yielded another 0.3 g of product. Total yield: 1.6 g; melting point 163.3° C.

(D) 4,5-Bis(phenylmethoxy)-2-pyridinamine, trifluoroacetate (1:1) salt 1.52 g of [4,5-Bis(phenylmethoxy)-2-pyridinyl]carbamic acid, 1,1-dimethylethyl ester (3.75 mmol) was dissolved in a mixture of 1.3 g of anisole and 18 ml of trifluoroacetic acid. After stirring for 2 hours at room temperature, the volatile reagents were evaporated in vacuo and the residual oil triturated with ether to yield 1.28 g of product; melting point 183.2° C.

(E) 4,5-Bis(phenylmethoxy)-2-pyridinamine 0.71 g (1.7 mmol) of 4,5-bis(phenylmethoxy)-2-pyridinamine, trifluoroacetate (1:1) salt was added to a solution of 0.1 g (2.5 mmol) of sodium hydroxide in 10 ml of water. The mixture was layered with 10 ml of ethyl acetate and stirred intensively for 5 minutes. The organic layer was separated, dried over sodium sulfate and evaporated to yield an oil which crystallized on standing. The crystals were triturated with petroleum ether and dried in vacuo. Yield: 0.43 g; melting point 111°–113° C.

(F) [[[4,5-Bis(phenylmethoxy)-2-pyridinyl]amino]methylene]malonic acid, diethyl ester A suspension of 4,5-bis(phenylmethoxy)-2-pyridinamine (8.7 g, 28.4 mmol) in diethyl ethoxymethylenemalonate (61.4 g, 284.0 mmol) was heated to 120° C. (bath temperature) for 2 hours. The major part of the diethyl ethoxymethylenemalonate was distilled off in vacuo and 100 ml of ether was added after cooling. The mixture was stored in the refrigerator overnight. The resulting crystals were filtered off with suction, washed with ether and dried in vacuo. Yield: 10.81 g; melting point 117.3° C.

(G) 4-Oxo-7,8-bis(phenylmethoxy)-4H-pyrido[1,2-a]pyrimidine-3-carboxylic acid, ethyl ester At 225° C. [[[4,5-bis(phenylmethoxy)-2-pyridinyl]amino]methylene]malonic acid, diethyl ester (10.7 g, 22.45 mmol) was added to 135 g of diphenylether. After stirring for 30 minutes at 225° C., the mixture was allowed to cool at room temperature, and 150 ml of petroleum ether was added. After standing overnight in the refrigerator, the resulting crystals were collected by filtration, washed with petroleum ether and recrystallized from ethanol. Yield: 4.77 g; melting point 175.3° C.

(H) 4-Oxo-7,8-bis(phenylmethoxy)-4H-pyrido[1,2-a]pyrimidine-3-carboxylic acid 20.3 ml of 1N sodium hydroxide solution was added to a solution of 4-oxo-7,8-bis(phenylmethoxy)-4H-pyrido[1,2-a]pyrimidine-3-carboxylic acid, ethyl ester (6.61 g, 15.36 mmol) in 240 ml of water:tetrahydrofuran 1:1). After stirring overnight at 40° C., 200 ml of water was added, and the pH was adjusted to 2 with 3N hydrochloric acid. The resulting precipitate was filtered off with suction, washed with water and dried in vacuo. Yield: 5.28 g; melting point 207.8° C.

(I) 4-Oxo-7,8-bis(phenylmethoxy)-4H-pyrido[1,2-a]pyrimidine-3-carbonyl chloride

To a suspension of 4-oxo-7,8-bis(phenylmethoxy)-4H-pyrido[1,2-a]pyrimidine-3-carboxylic acid (1.21 g, 3.0 mmol) in 30 ml of dichloromethane was added 0.69 g (3.3 mmol) of phosphorous pentachloride at 0° C. After stirring for 90 minutes, the solid was filtered off, washed with dichloromethane and dried in vacuo. Yield: 0.91 g; melting point 152.4° C.

(J) [1-[[[[3-[[[4-Oxo-7,8-bis(phenylmethoxy)-4H-pyrido[1,2-a]pyrimidin-3-yl]carbonyl]amino]-2-oxo-1-imidazolidinyl]sulfonyl]amino]carbonyl]-2-oxo-3-azetidinyl]carbamic acid, phenylmethyl ester N-Methyl-N-trimethylsilyl trifluoroacetamide (2.39 g, 12.0 mmol) was added to a suspension of [1-[[[(3-amino-2-oxo-1-imidazolidinyl)sulfonyl]amino]carbonyl]-2-oxo-3-azetidinyl[carbamic acid, phenylmethyl ester, trifluoroacetate (1:1) salt (1.05 g, 2.0 mmol) in 20 ml of acetonitrile. After stirring for 1 hour at room temperature, the volatiles were distilled off in vacuo, and the residue taken up in 20 ml of tetrahydrofuran. N-Methyl-N-trimethylsilyl trifluoracetamide (0.8 g, 4.0 mmol) was added, followed by 4-oxo-7,8-bis-(phenylmethoxy)-4H-pyrido[1,2-a]pyrimidine-3-carbonyl chloride (0.84 g, 2.0 mmol). After stirring overnight at room temperature, the precipitate was filtered off, washed with ether and triturated with water to give 0.3 g of product. The mother liquor was evaporated to dryness, and the residue triturated with water to give another 1.14 g. Total yield: 1.44 g.

(K) 2-[[[1-(2-Amino-4-thiazolyl)-2-[[1-[[[3-[[(7,8-dihydroxy-4-oxo-4H-pyrido[1,2-a]pyrimidin-3-yl)carbonyl]amino]-2-oxo-1-imidazolidinyl]-sulfonyl]amino]carbonyl]-2-oxo-3-azetidinyl]amino]-2-oxoethylidene]-amino]oxy]-2-methylpropanoic acid, diphenylmethyl ester To a solution of [1-[[[[3-[[[4-oxo-7,8-bis(phenylmethoxy)-4H-pyrido[1,2-a]pyrimidin-3-yl]carbonyl]amino]-2-oxo-1-imidazolidinyl]sulfonyl]amino]carbonyl]-2-oxo-3-azetidinyl]carbamic acid, phenylmethyl ester (1.35 g, 1.66 mmol) in 65 ml of N,N-dimethylformamide, N-methyl-N-trimethylsilyl trifluoroacetamide (1.66 g, 8.33 mmol) was added. After 20 minutes 0.45 g of palladium on carbon was added, and the mixture was hydrogenolyzed for 1 hour. The catalyst was removed by filtration, and to the filtrate (Z)-2-amino-α-[[2-(diphenylmethoxy)-1,1-dimethyl-2-oxoethoxy]imino]-4-thiazoleacetic acid, 1-benzotriazole ester (0.83 g, 1.5 mmol) was added. After stirring overnight, the solvent was distilled off, and the residue triturated with 20 ml of water. The resulting solid was filtered off with suction and dried in vacuo. Yield of crude product: 1.28 g.

(L)
[3S(Z)]-2-[[[1-(2-Amino-4-thiazolyl)-2-[[1-[[[[3-[[( 7,8-dihydroxy-4-oxo-4H-pyrido[1,2-a]pyrimidin-3-yl)carbonyl]amino]-2-oxo-1-imidazolidinyl]sulfonyl]amino]carbonyl-2-oxo-3-azetidinyl]amino]-2-oxoethylidene]amino]oxy]-2-methylpropanoic acid, disodium salt To a suspension of 2-[[[1-(2-amino-4-thiazolyl)-2-[[1-[ [[[-3-[[7,8-dihydroxy-4-oxo-4H-pyrido[1,2-a]-pyrimidin-3-yl)carbonyl]amino]-2-oxo-1-imidazolidinyl]-sulfonyl]amino]carbonyl]-2-oxo-3-azetidinyl]amino]-2-oxoethylidene]amino]oxy]-2-methylpropanoic acid, diphenylmethyl ester (1.2 g, 1.35 mmol) in 1.2 ml of anisole, 12 ml trifluoroacetic acid was added dropwise at 0° C. After stirring for 1 hour, 100 ml of ether was added, and the resulting precipitate was filtered off, washed with ether and dried in vacuo. The salt was suspended in water and the pH brought to 6 with 2N sodium hydroxide solution. Freeze drying yielded 1.31 g of crude product which was chromatographed twice on Organogen under mplc conditions with water as eluent. Freeze drying of the sample containing fractions yielded 93 mg of the title compound; melting point >300° C.

EXAMPLE 7

[3S(Z)]-2-[[[1-(2-Amino-4-thiazolyl)-2-[[1-[[[[3-[[(6,7--dihydroxy-3-isoquinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt (A) 1,2,3,4-Tetrahydro-6,7-dihydroxy-3-isoquinoline carboxylic acid To a solution of L-3-(3,4-dihydroxphenyl)alanine (20 g, 101.4 mmol) in 1200 ml of 0.5N sulfuric acid was added 120 ml of formaldehyde (37 weight percent solution in water). After stirring overnight at room temperature, the pH was brought to 4.0-4.2 with 2N sodium hydroxide (about 260 ml) under ice cooling. A further increase of the pH caused decomposition of the product. While stirring at 3° C., the solution became turbid. To complete the crystallization, the mixture was stored in the refrigerator overnight. The crystals were collected by filtration, washed with water and dried in vacuo. Yield: 13.93 g; melting point 287.9° C.

(B) 1,2,3,4-Tetrahydro-6,7-dihydroxy-3-isoquinolinecarboxylic acid, methyl ester, hydrochloride At 40° C., a steam of gaseous hydrogen chloride was bubbled through a solution of 1,2,3,4-tetrahydro-6,7-dihydroxy-3-isoquinolinecarboxylic acid (32.4 g, 155.0 mmol) in 1.5 l of methanol for 2 hours. After stirring overnight at room temperature, the solvent was distilled off in vacuo and the residue triturated with ether to furnish 38.95 g of the product. Melting point 204.8° C.

(C) 3,4-Dihydro-6,7-dihydroxy-2,3(1H)isoquinolinedicarboxylic acid, 3-methyl, 1-(phenylmethyl) ester To a solution of 1,2,3,4-tetrahydro-6,7-dihydroxy-3-isoquinolinecarboxylic acid, methyl ester hydrochloride salt (30.1 g, 115.9 mmol) in 1230 ml of water-tetrahydrofuran 1:1 were added benzyl chloroformate (19.8 g, 115.9 mmol) and 2N sodium hydroxide solution at pH 8 dropwise to keep the pH at 8. After 2 hours, the pH was brought to 2 with 5N hydrochloric acid. Tetrahydrofuran was distilled off in vacuo and the aqueous phase was extracted three times with ethyl acetate. The combined organic layers were stirred with activated carbon, dried over sodium sulfate and evaporated in vacuo to give 41.6 g of a yellow foam.

(D) 3,4-Dihydro-6,7-dimethoxy-2,3(1H)isoquinolinedicarboxylic acid, 3-methyl, 1-(phenylmethyl) ester To a solution of 3,4-dihydro-6,7-dihydroxy-2,3(1H)-isoquinolinedicarboxylic acid, 3-methyl, 1-(phenylmethyl) ester (41.2 g, 115.2 mmol) in 1680 ml of water-tetrahydrofuran 1:1 were added simultaneously under ice cooling, dimethylsulfate (35.36 g, 280.4 mmol) and potassium hydroxide (18.5 g (85%), 280.4 mmol) dissolved in 420 ml of water. After stirring overnight at room temperature, the pH was brought to 1-2 with 5N hydrochloric acid. Tetrahydrofuran was distilled off in vacuo and the aqueous phase was extracted three times with ether. The combined organic layers were stirred with activated carbon, dried over sodium sulfate and evaporated to give 39.4 g of a yellow foam.

(E) 1,2,3,4-Tetrahydro-6,7-dimethoxy-3-isoquinolinecarboxylic acid, methylester 3,4-Dihydro-6,7-dimethoxy-2,3-(1H)-isoquinolinedicarboxylic acid, 3-methyl, 1-(phenylmethyl) ester (39.4 g, 102.3 mmol), dissolved in 1300 ml of N,N-dimethylformamide, was hydrogenated over 13 g of palladium on activated carbon for 80 minutes. The catalyst was removed by filtration and the solvent evaporated in vacuo. Yield: 22.68 g brown oil (contains N,N-dimethylformamide).

(F) 6,7-Dimethoxy-3-isoquinolinecarboxylic acid, methyl ester

To a solution of 1,2,3,4-tetrahydro-6,7-dimethoxy-3-isoquinolinecarboxylic acid, methyl ester (19.77 g, 78.7 mmol) in 400 ml of tetrahydrofuran, 2,3-dichloro-5,6-dicyano-1,4-benzoquinone (39.3 g, 173.1 mmol) was added. The dark solution was heated under reflux overnight. The resulting precipitate was filtered off, dissolved in 500 ml dichloromethane/water 1:1, and the pH was adjusted to 10 by means of 1N sodium hydroxide. The phases were separated, the aqueous phase extracted once with dichloromethane and the combined organic phases washed twice with 100 ml of water containing a few drops of 1N sodium hydroxide. After the drying and evaporating of the solvent, 9.20 g of the title compound was obtained; melting point 214.9° C.

(G) 6,7-Dimethoxy-3-isoquinolinecarboxylic acid

A solution of sodium hydroxide (4.38 g, 109.4 mmol) in 70 ml of water was added to a solution of 6,7-dimethoxy-3-isoquinolinecarboxylic acid, methyl ester (22.54 g, 91.2 mmol) in 1800 ml of water:tetrahydrofuran 1:1. After stirring overnight at room temperature, the tetrahydrofuran was distilled off in vacuo and the pH of the remaining aqueous solution was brought to 3 with 3N hydrochloric acid. The resulting precipitate was filtered off with suction, washed with water and dried in vacuo. Yield: 19.57 g; melting point 228.2° C.

(H)
6,7-Dimethoxy-N-(2-oxo-1-imidazolidinyl)-3-isoquinolinecarboxamide

To a solution of 6,7-dimethoxy-3-isoquinolinecarboxylic acid (6.99 g, 30.0 mmol) in 300 ml of N,N-dimethylformamide were added triethylamine (12.14 g, 120.0 mmol) and diphenyl chlorophosphate (80.6 g, 30.0 mmol) at 0° C. After stirring for 4 hours at 0° C., N-amino-2-oxoimidazolidine (3.03 g, 30.0 mmol) was added, and the mixture was stirred at 0° C. overnight. Ammonium salts (2.0 g) were filtered off, and the filtrate was evaporated in vacuo. The residue was triturated with a 1:1 mixture of water and ethyl acetate. The solid was filtered off and triturated twice with water at pH 8 for 3 hours. The remaining solid was filtered off, washed with water and dried in vacuo. Yield: 4.30 g; melting point 220° C. (dec.).

(I)
6,7-Dihydroxy-N-(2-oxo-1-imidazolidinyl)-3-isoquinolinecarboxamide

A solution of boron tribromide (10.22 g, 40.8 mmol) in 100 ml of dichloromethane was added dropwise at −78° C. to a solution of 6,7-dimethoxy-N-(2-oxo-imidazolidinyl)-3-isoquinolinecarboxamide (4.30 g, 13.6 mmol) in 100 ml of dichloromethane. The mixture was allowed to warm to room temperature and was stirred overnight. The resulting solid was filtered off with suction, taken up in methanol and stirred for 1 hour. The methanol was distilled off in vacuo and the residue triturated with ether to give the crude product which was again treated with boron tribromide (3 equivalents) and methanol as described above to get a complete reaction. YIeld: 3.82 g; melting point 220° C. (dec.).

(J)
[1-[[[[-3-[[(6,7-Dihydroxy-3-isoquinolinyl)carbonyl]amino]-2-oxo-1-imidazolidinyl]sulfonyl]amino]carbonyl]-2-oxo-3-azetidinyl]carbamic acid, phenylmethyl ester, monosodium salt To a suspension of (S)-3-[[(phenylmethoxy)carbonyl]amino]-2-oxo-1-azetidine (1.10 g, 5.0 mmol) in 25 ml of ethylacetate, chlorosulfonyl isocyanate (0.71 g, 5.0 mmol) was added, and the mixture was stirred for 1 hour at room temperature (solution A). To a solution of 6,7-dihydroxy-N-(2-oxo-1-imidazolidinyl)-3-isoquinolinecarboxamide (1.44 g, 5.0 mmol) in 25 ml of ethyl acetate, N-methyl-N-trimethylsilyltrifluoroacetamide (4.99 g, 25.0 mmol) was added. After stirring for 1 hour at 40° C., a clear solution was obtained. The solution was cooled and added to solution A at 0° C. After stirring overnight at room temperature, 500 ml of water was added whereupon a gummy residue separated. The mother liquor was decanted and the residue triturated with ether to give a solid which was filtered off, washed with ether and dried in vacuo (2.30 g). The solid was suspended in water, the pH brought to 6 with 2N sodium hydroxide and the solution freeze dried. Yield 1.65 g.

(K)
2-[[[1-(2-Amino-4-thiazolyl)-2-[[1-[[[[3-[[(6,7-dihydroxy-3-isoquinolinyl)carbonyl]amino]-2-oxo-1-imidazolidinyl]sulfonyl]amino]carbonyl]-2-oxo-3-azetidinyl]-amino-2-oxoethylidene]amino]oxy]-2-methylpropanoic acid, diphenylmethyl ester To a solution of [1-[[[[3-[[(6,7-dihydroxy-3-isoquinolinyl)carbonyl]amino]-2-oxo-1-imidazolidinyl]-sulfonyl]amino]carbonyl]-2-oxo-3-azetidinyl]carbamic acid, phenylmethyl ester, monosodium salt (1.50 g, 2.44 mmol) in 70 ml of N,N-dimethylformamide, N-methyl-N-trimethylsilyl trifluoroacetamide (2.44 g, 12.22 mmol) was added under nitrogen protection. After 30 minutes 0.49 g of palladium on carbon was added, and the mixture was hydrogenolyzed for 1 hour. The catalyst was removed by filtration, and to the filtrate, (Z)-2-amino-α-[[2-(diphenylmethoxy)-1,1-dimethyl-2-oxoethoxy]imino]-4-thiazoleacetic acid, 1-benzotriazole ester.(1.22 g, 2.20 mmol) was added. After stirring overnight, the solvent was distilled off, and the residue triturated with water. The resulting solid was filtered off, triturated with ether and dried in vacuo. Yield: 1.75 g.

(L)
[3S(Z)]-2-[[[1-(2-Amino-4-thiazolyl)-2-[[1-[[[[-3-[[(6,-7-dihydroxy-3-isoquinolinyl)carbonyl]amino]-2-oxo-1-imidazolidinyl]sulfonyl]amino]carbonyl]-2-oxo-3-azetidinyl]amimo]-2-oxoethylidene]amino]oxy]-2-methylpropanoic acid, disodium salt To a suspension of 2-[[[1-(2-amino-4-thiazolyl)-2-[[ 1-[[[[3-[[(6,7-dihydroxy-3-isoquinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester (1.72 g, 1.91 mmol) in 2 ml of anisole, 20 ml of trifluoroacetic acid was added dropwise at 0° C. After stirring for 1 hour, 100 ml of ether was added, and the resulting solid was filtered off, washed with ether and dried in vacuo. The compound was suspended in water and the pH adjusted to 6 with 2N sodium hydroxide. After freeze drying the resulting solution, the salt was chromatographed on XAD with water and water-:acetonitrile 9:1 as eluents, to give, after freeze drying the sample containing fractions, 445 mg of the title compound which was chromatographed on Organogen. Yield after 2nd chromatography: 240 mg; melting point >300° C.

What is claimed is:
1. A compound having the formula

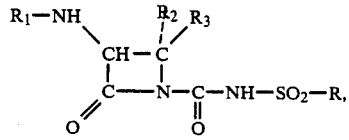

or a pharmaceutically acceptable salt thereof wherein R is

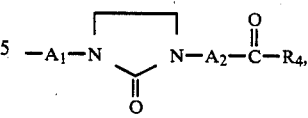

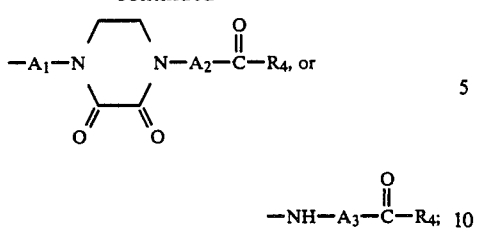

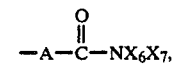

R₁ is an acyl group derived from a carboxylic acid;
R₂ and R₃ are the same or different and each is hydrogen, alkyl, alkenyl, alkynyl, cycloalkyl, phenyl, substituted phenyl or a 4, 5, 6 or 7-membered heterocycle or one of R₂ and R₃ is hydrogen and the other is azido, halomethyl, dihalomethyl, trihalomethyl, alkoxycarbonyl, 2-phenylethenyl, 2-phenylethynyl, carboxyl, —CH₂X₁, —S—X₂, —O—X₂,

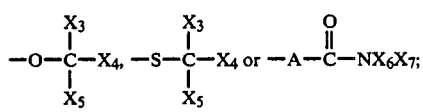

R₄ is

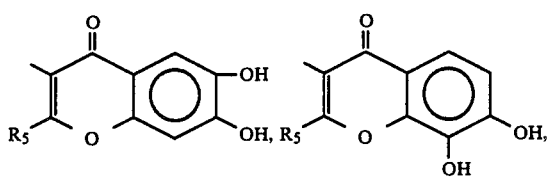

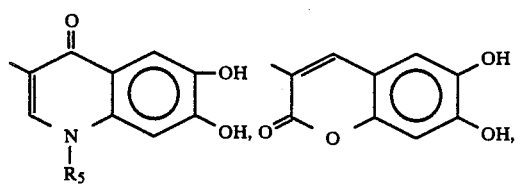

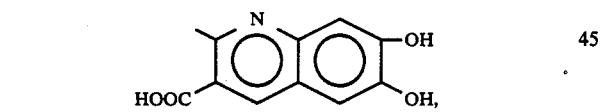

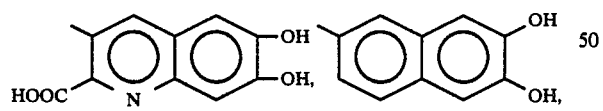

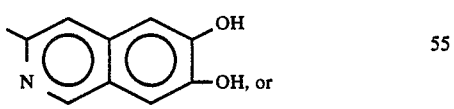

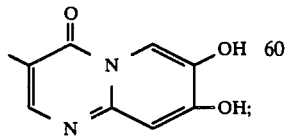

R₅ is hydrogen or alkyl of 1 to 4 carbon atoms;
X₁ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

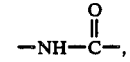

—S—X₂, or —O—X₂;

X₂ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl;

one of X₃ and X₄ is hydrogen and the other is hydrogen or alkyl, or X₃ and X₄ when taken together with the carbon atom to which they are attached form a cycloalkyl group;

X₅ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

X₆ and X₇ are the same or different and each is hydrogen, alkyl, phenyl or substituted phenyl, or X₆ is hydrogen and X₇ is amino, substituted amino, alkanoylamino or alkoxy, or X₆ and X₇ when taken together with the nitrogen atom to which they are attached form a 4, 5, 6 or 7-membered heterocycle;

A is —CH=CH—, —(CH₂)ₘ—, —(CH₂)ₘ—O—, —(CH₂)ₘ—NH— or —CH₂—S—CH₂—;
m is 0, 1 or 2;
A₁ is a single bond,

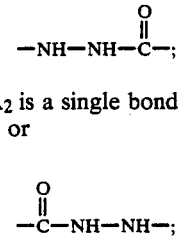

—NH— or

—NH—NH—C(O)—;

A₂ is a single bond, —NH—, —CH₂—CH₂—NH—, or

—C(O)—NH—NH—;

and
A₃ is —NH—, —(CH₂)ᵧ—NH—,

—NH—C(O)—NH—NH—, —C(O)—NH—NH—, or —N(CH₂X)— wherein X is hydrogen, carboxyl or carbamoyl and y is 2, 3, or 4;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, alkanoyloxy, aminocarbonyl, or carboxy groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "a 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "substituted amino" refers to a group having the formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein R is

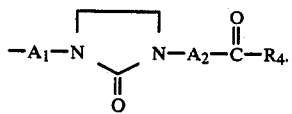

3. A compound in accordance with claim 1 wherein R is

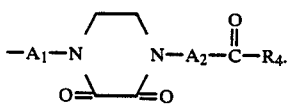

4. A compound in accordance with claim 1 wherein R is

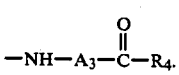

5. A compound in accordance with claim 1 wherein $R_2$ and $R_3$ are each hydrogen.

6. A compound in accordance with claim 2 wherein $R_2$ and $R_3$ are each hydrogen.

7. A compound in accordance with claim 2 wherein R is

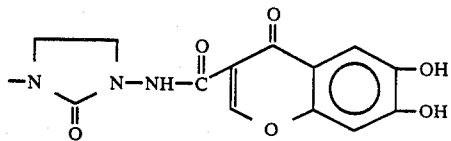

8. A compound in accordance with claim 2 wherein R is

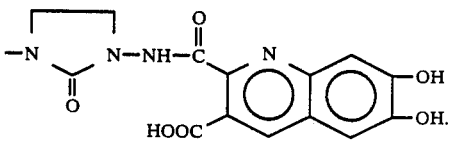

9. A compound in accordance with claim 2 wherein R is

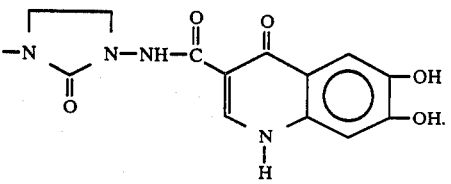

10. A compound in accordance with claim 1 wherein $R_1$ is

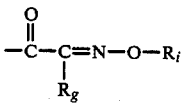

and $R_g$ is 2-amino-4-thiazolyl and $R_i$ is methyl, ethyl, carboxymethyl, 1-carboxy-1-methylethyl, 1-carboxy-1-ethyl, or

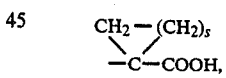

wherein s is 1, 2 or 3.

11. A compound in accordance with claim 1 wherein $R_1$ is

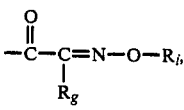

$R_g$ is 2-amino-4-thiazolyl and $R_i$ is carboxymethyl, 1-carboxy-1-methylethyl, 1-carboxy-1-ethyl, or

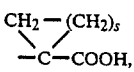

wherein s is 1, 2 or 3.

12. A compound in accordance with claim 2 wherein $R_1$ is

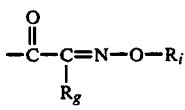

and $R_g$ is 2-amino-4-thiazolyl and $R_i$ is methyl, ethyl, carboxymethyl, 1-carboxy-1-methylethyl, 1-carboxy-1-ethyl or

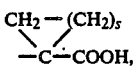

wherein s is 1, 2 or 3.

13. A compound in accordance with claim 2 wherein $R_1$ is

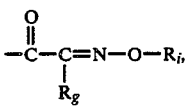

$R_g$ is 2-amino-4-thiazolyl and $R_i$ is carboxymethyl, 1-carboxy-1-methylethyl, 1-carboxy-1-ethyl or

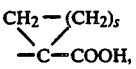

wherein s is 1, 2 or 3.

14. The compound in accordance with claim 1, 2-[[[1-(2-amino-4-thiazolyl)-2-[[1-[[[[3-[[(1,4-dihydro-6,7-dihydroxy-4-oxo-3-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, or a pharmaceutically acceptable salt thereof.

15. The compound in accordance with claim 1, [3S-(Z)]-2-[[[1-(2-amino-4-thiazolyl)-2-[[1-[[[[3-[[(6,7-dihydroxy-4-oxo-4H-benzo[b]pyran-3-yl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, or a pharmaceutically acceptable salt thereof.

16. The compound in accordance with claim 1, 2-[[[1-(2-amino-4-thiazolyl)-2-[[1-[[[[3-[[(3-carboxy-6,7-dihydroxy-2-quinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, or a pharmaceutically acceptable salt thereof.

17. The compound in accordance with claim 1, [3S(Z)]-2-[[[1-(2-amino-4-thiazolyl)-2-[[1-[[[[2-[(6,7-dihydroxy-2-naphthalenyl)carbonyl]hydrazino]sulfonyl]amino]carbonyl]-2-oxo-3-azetidinyl]amino]-2-oxoethylidene]amino]oxy]-2-methyl propanoic acid, or a pharmaceutically acceptable salt thereof.

18. The compound in accordance with claim 1, [3S(Z)]-2-[[[3-[[[[3-[[(2-amino-4-thiazolyl)(methoxyimino)acetyl]amino]-2-oxo-1-azetidinyl]carbonyl]amino]sulfonyl]-2-oxo-1-imidazolidinyl]amino]carbonyl]-6,7-dihydroxy-3-quinolinecarboxylic acid, or a pharmaceutically acceptable salt thereof.

19. The compound in accordance with claim 1, [3S(Z)]-2-[[[1-(2-amino-4-thiazolyl)-2-[[1-[[[[3-[[(7,8-dihydroxy-4-oxo-4H-pyrido[1,2-a]pyrimidin-3-yl)carbonyl]amino]-2-oxo-1-imidazolidinyl]sulfonyl]amino]carbonyl-2-oxo-3-azetidinyl]amino]-2-oxoethylidene]amino]oxy]-2-methylpropanoic acid, or a pharmaceutically acceptable salt thereof.

20. The compound in accordance with claim 1, [3S(Z)]-2-[[[1-(2-amino-4-thiazolyl)-2-[[1-[[[[3-[[(6,7-dihydroxy-3-isoquinolinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, or a pharmaceutically acceptable salt thereof.

* * * * *